United States Patent [19]

Liotta et al.

[11] Patent Number: 5,432,273

[45] Date of Patent: * Jul. 11, 1995

[54] PREPARATION OF 3'-SUBSTITUTED-2',3'-DIDEOXYNUCLEOSIDES AND 2'-DEOXYNUCLEOSIDES FROM ACYCLIC, ACHIRAL PRECURSORS

[75] Inventors: Dennis C. Liotta, Stone Mountain; Michael W. Hager, Atlanta, both of Ga.

[73] Assignee: Emory University, Atlanta, Ga.

[*] Notice: The portion of the term of this patent subsequent to Apr. 26, 2011 has been disclaimed.

[21] Appl. No.: 960,762

[22] Filed: Oct. 14, 1992

Related U.S. Application Data

[63] Continuation-in-part of Ser. No. 681,109, Apr. 5, 1991.

[51] Int. Cl.$^6$ .............................................. C07H 19/06
[52] U.S. Cl. ............................... 536/26.71; 536/27.14; 536/28.2
[58] Field of Search .................. 536/26.71, 27.14, 28.2

[56] References Cited

PUBLICATIONS

Caron, M., et al., "Ti(O-i-Pr)$_4$-Mediated Nucleophilic Openings of 2,3-Epoxy Alcohols. A Mild Procedure for Regioselective Ring-Opening," *J. Org. Chem.*, vol. 50, No. 9 (1985) pp. 1557-1560.

Gao, Y., et al. "Catalytic Asymmetric Epoxidation and Kinetic Resolution: Modified Procedures Including in Situ Derivation," *J. Am. Chem. Soc.*, vol. 109, (1987), pp. 5765-5780.

Jacobesen, E. N., et al., "Asymmetric Dihydroxylation via Lagand-Accelerated Catalysis", *J. Am. Chem. Soc.*, vol. 110, No. 6 (1988) 1968-1970.

Kwong, H., et al., "Preclusion of the 'Second Cycle' in the Osmium-Catalyzed Asymmetric Dihydroxylation of Olefins Leads to a Superior Process," *Tetrahedron Letters*, vol. 31, No. 22 (1990) pp. 2999-3002.

Labelle, M., et al., "Homoallylic Chiral Induction in the Synthesis of 2,4-Disubstituted Tetrahydrofurans by Iodoetherification, Synthetic Scope and Chiral Induction Mechanism," *J. Am. Chem. Soc.*, vol. 110, (1988) pp. 4533-4540.

Marshall, J. A. et al., "Condensation of Long-Chain α-Phosphono Carboxylates with Aldehydes," *J. Org. Chem.*, vol. 51, No. 10 (1986) pp. 1735-1741.

Maryanoff, B. E., et al., "The Wittig Olefination Reaction and Modifications Involving Phosphoryl-Stabilized Carbanions, Stereochemistry, Mechanism, and Selected Synthetic Aspects," *Chem. Rev.*, vol. 89 (1989) pp. 863-927.

Nagaoka, H., et al., "Further Synthetic Studies on Rifamycin S$^1$," *Tetrahedron Letters*, vol. 37, No. 23 (1981) pp. 3873-3888.

Vorbrüggen, H., et al., "Nucleoside Synthesis with Trimethylsilyl Triflate and Perchlorate as Catalysts," *Chem. Ber.*, vol. 114 (1981) pp. 1234-1255.

*Primary Examiner*—Che S. Chereskin
*Attorney, Agent, or Firm*—Kilpatrick & Cody

[57] ABSTRACT

A process for the preparation of 3'-substituted-2',3'-dideoxynucleosides is provided that utilizes inexpensive, non-carbohydrate, acyclic, achiral starting materials and that proceeds with high enantiomeric and stereochemical control. The method can be used to prepare the pharmaceutically important compounds 3'-azido-3'-deoxythymidine, 3'-azido-2',3'-dideoxyuridine, 3'-fluoro-3'-deoxythymidine, and 3'-fluoro-3'-deoxyuridine.

22 Claims, 4 Drawing Sheets

33

34

35

PREPARATION OF 3'-SUBSTITUTED-2',3'-DIDEOXYNUCLEOSIDES AND 2'-DEOXYNUCLEOSIDES FROM ACYCLIC, ACHIRAL PRECURSORS

The government has rights in this invention by virtue of a grant from the National Institute of Health that partially funded research leading to this invention.

BACKGROUND OF THE INVENTION

This application is a continuation-in-part of U.S. Ser. No. 07/681,109, entitled "Preparation of 3'-Substituted-2',3'-Dideoxynucleosides and 2'-Deoxynucleosides from Acyclic, Achiral Precursors," filed on Apr. 5, 1991, by Dennis C. Liotta and Michael W. Hager.

This invention is in the area of organic synthesis of nucleosides, and in particular is-directed to a highly stereoselective process for the preparation of 3'-substituted-2',3'-dideoxynucleosides and 2'-deoxynucleosides from acyclic, achiral precursors.

In 1985, it was reported that the synthetic nucleoside 3'-azido-3'-deoxythymidine (AZT) inhibits the replication of human immunodeficiency virus type 1 (referred to below as HIV), the etiological cause of acquired immune deficiency syndrome (AIDS). Since then, a number of other synthetic nucleosides, including 3'-fluoro-3'-deoxythymidine (FLT) and 3'-azido-2',3'-dideoxyuridine (AZDU), have proven to be effective against HIV. A number of other 2',3'-dideoxynucleosides have been demonstrated to inhibit the growth of a variety of other viruses in vitro. It appears that, after cellular phosphorylation to the 5'-triphosphate by cellular kinases, these synthetic nucleosides are incorporated into a growing strand of viral DNA, causing chain termination. 3'-Azido-3'-deoxythymidine is a potent inhibitor of HIV reverse transcriptase and is presently the only drug that has been approved by the FDA for the treatment of AIDS.

2',3'-Dideoxynucleosides have historically been prepared by either of two routes; deoxygenation and derivatization of an intact nucleoside, or condensation of a derivatized sugar moiety with a nitrogenous base.

The original synthesis of 3'-substituted-2',3'-dideoxynucleosides from 2'-deoxynucleosides by Horwitz et al. illustrates the first approach: the modification of intact nucleosides by altering the carbohydrate moiety (see Scheme I below). Horwitz, J.P.; Chua, J.; Noel, M. J. Org. Chem. 29, 2076 (1964); Horwitz, J.P.; Chua, J.; Urbanski, J.A.; Noel, M. J. Org. Chem., 28, 942 (1963); and Horwitz, J.P.; Chua, J.; Urbanski, J.A. J. Org Chem., 27, 3300 (1962). Horwitz prepared AZT by replacement of the 3'-hydroxyl group of thymidine with azide in a four step process with retention of stereochemistry. The advantages of this approach are numerous. It is short, efficient and proceeds with a high degree of stereocontrol. The major disadvantage is that the high cost of the starting material, 2'-deoxynucleoside, makes the overall process expensive.

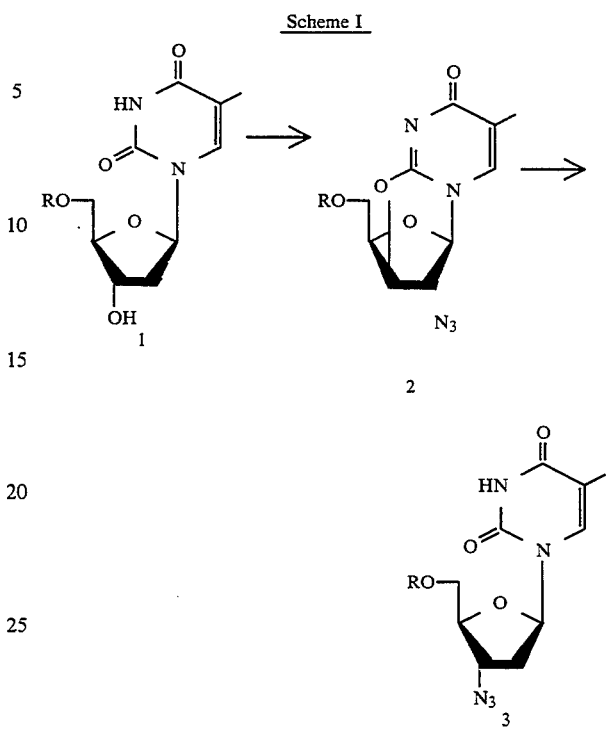

Scheme I

The second general approach is illustrated by the synthesis of AZT and AZDU, by Chu, et al.. Chu, C.K., et al., Tetrahedron Lett., 29, 5349 (1988); U.S. Pat. No. 4,987,224. Starting from D-mannitol, a derivatized ribose is prepared in eight steps, that, when exposed to Vorbruggen coupling conditions with a protected thymidine or uridine followed by deprotection, forms a 1:1 α to β anomeric mixture of AZT (or AZDU). (See Scheme II below.)

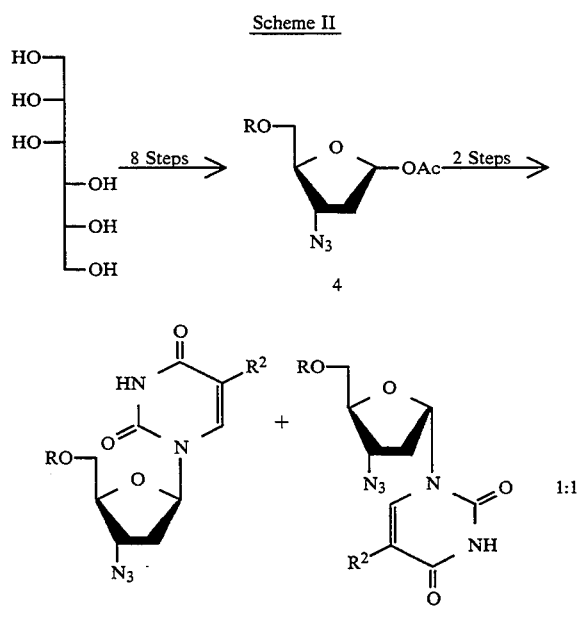

Scheme II $R^2 = CH_3$  3
$R^2 = H$  6

The β-anomeric nucleoside is more biologically active than the α-anomeric nucleoside, and must be isolated from the mixture through a chromatographic separation.

Most of the other reported methods of preparation of nucleosides are suitable only as laboratory syntheses to obtain small amounts of compound for experimental use, but are not well suited for industrial scale preparation of the compounds, because of the number of steps required to obtain the product and or the cost of the nucleoside starting material.

Several laboratory-scale syntheses of 3'-fluoro-3'-deoxythymidine have been reported. Motawia, M.S.; Pedersen, E.B. Liebigs Ann. *Chem.* 1990, 1137; Green, K.; Blum, D.M. *Tetrahedron Lett.* 1991, 32, 2091. None of them appear to be suitable for large scale manufacturing of the compound, in large part because the syntheses make use of fluorinating reagents, such as anhydrous HF and DAST (diethylamino sulfur trifluoride), which are difficult to handle on a large scale.

The problems described above that are encountered in the preparation of pharmaceutically active nucleosides increase the public cost of health care and result in shortages of severely needed antiviral compounds. In fact, the high cost of the antiviral, and in particular anti-HIV, nucleosides prevents many of those in need from being able to obtain the drug at all.

Therefore, it is an object of the present invention to provide a synthesis of 3'-substituted-2',3'-dideoxynucleosides and 2'-deoxynucleosides from inexpensive, readily available starting materials.

It is another object of the present invention to provide a synthesis of 3'-substituted-2',3'-dideoxynucleosides and 2'-deoxynucleosides that does not result in the production of a significant amount of undesired isomers or anomers.

SUMMARY OF THE INVENTION

A process for the preparation of 3'-substituted-2',3'-dideoxynucleosides and 2'-deoxynucleosides is provided that utilizes inexpensive, non-carbohydrate, acyclic, achiral starting materials and that proceeds with high enantiomeric and stereochemical control. This process represents a significant advance in the art of preparation of biologically active nucleosides, in that after addition of the heterocyclic base, the achiral precursor is cyclized with complete or virtually complete stereospecificity to the desired, biologically active β-anomeric nucleoside. It is believed that this is the first report of a synthesis of a nucleoside in which the stereochemistry of the glycosidic linkage is controlled during cyclization. The high degree of stereocontrol throughout the synthesis may decrease the cost of the product relative to other known methods of manufacture of 3'-deoxy-2',3'-dideoxynucleosides or 2'-deoxynucleosides. Further, the reagents used in the synthesis can be prepared easily on large scale from inexpensive materials.

The starting material for this process is 5,5-di(protected)oxy-2E-penten-1-ol, that can be conveniently prepared in a number of ways from readily available reagents. The penten-1-ol is epoxidized to the 2(R), 3(S) epoxy alcohol, preferably under Sharpless asymmetric conditions. The C-2, C-3 epoxy group is then opened and a nucleophile inserted at the C-3 position, to provide a 3-(S)-substituted-5,5-di(protected)oxy-1,2-(S)-pentanediol. A 3'-substituted-2',3'-dideoxynucleoside is the final product when the nucleophile inserted in the C-3 position of the epoxy alcohol is other than hydroxyl. A 2'-deoxynucleoside is the final product when the nucleophile inserted into the C-3 position of the epoxy alcohol is hydroxyl or a group that can be cleaved to a hydroxyl group.

In a preferred embodiment of the invention, the desired heterocyclic base is then added to the 5-position of the pentanediol to produce a 5-(protected)oxy-5-(heterocyclic base)-3(S)-substituted-1,2-(S)-pentanediol. A key step in this process is the stereoselective cyclization of this pentanediol to form a 3'-α-substituted-2',3'-dideoxy-β-anomeric nucleoside or a 2'-deoxy-β-anomeric nucleoside under kinetic conditions in a protic acid or with a mild Lewis acid.

In another embodiment of this invention, the 3-(S)-substituted-5-di(protected)oxy-1,2-(S)-pentanediol is cyclized to form a 3-substituted-1-(α or β)-protected-(oxy)-4-hydroxymethyltetrahydrofuran, that is then reacted with a protected heterocyclic base to form the 3'-substituted-2',3'-dideoxynucleoside.

This process can be used to prepare a wide range of 3'-substituted-2',3'-dideoxynucleosides, through the selection of the nucleophile to be inserted in the 3'-position as well as selection of the heterocyclic base. The method can be used to prepare the pharmaceutically important compounds 3'-azido-3'-deoxythymidine, 3'-azido-2',3'-dideoxyuridine, 3'-fluoro-3'-deoxythymidine, and 3'-fluoro-3'-deoxyuridine. The method can also be used to prepare a wide range of 2'-deoxynucleosides, through selection of the heterocyclic base, including thymidine.

DETAILED DESCRIPTION OF THE INVENTION

Figure 1:
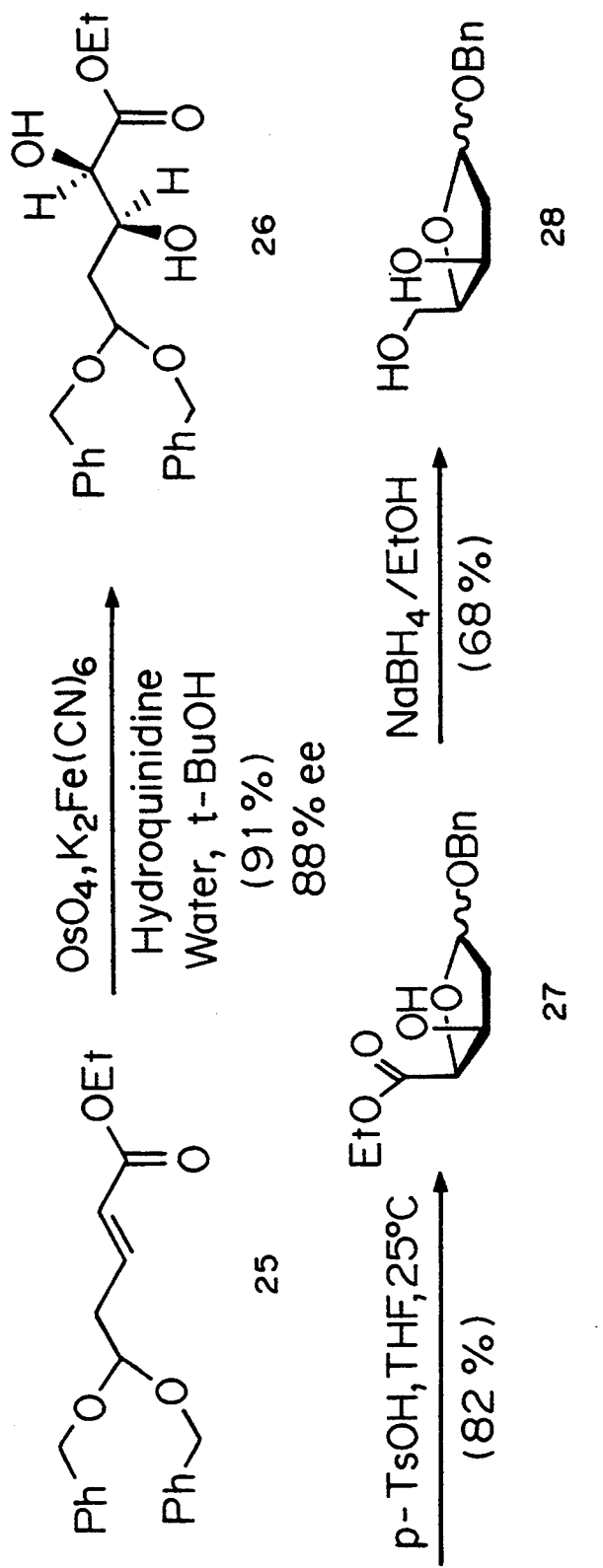
FIG. 1 is an illustration of the preparation of a lyxose carbohydrate derivative by the asymmetric dihydroxylation of 5,5-(diprotected oxy)-2E-pentanoate to form a 5,5-di(protected oxy)-2(R),3(S)-pentanoate followed by the stereoselective cyclization of the pentanoate to a 2'-deoxynucleoside in which the 3'-hydroxyl group of the carbohydrate is in the β, or lyxose, configuration.

As used herein, the term "3'-substituted nucleophile" refers to a compound in which a nucleophile, including but not limited to azido, amino, a mono- or di(aliphatic-)amine, such as mono- or diethylamine or diallylamine, nitro, chloro, fluoro, cyano, alkoxy, phenoxy, hydroxy, alkyl or aromatic mercaptyl, thiophenyl, selenium phenyl, acetylenic, thiocyano, allyloxy, bromo, benzoyl, acetyl, alkyl carboxylic acids, or LPTS (2,6-lutidine p-toluene sulfonate) is in the 3-position of the nucleoside.

The term "nucleophile" refers to an electron rich compound or moiety that will attack an electron deficient carbon atom.

The term "protected" refers to a group that is added to an oxygen or nitrogen atom to prevent its further reaction during the course of derivatization of other moieties in the molecule in which the oxygen or nitrogen is located. A wide variety of oxygen and nitrogen protecting groups are known to those skilled in the art of organic synthesis.

tween an appropriate C-2 or C-3 aldehyde or ketone with a suitable C-2 or C-3 Wittig-type phosphorus ylide reagent that results in a C-5 $\alpha,\beta$-unsaturated aidehyde, acid or ester. For a comprehensive review of the Wittig reaction and its recent modifications, see Chem. Rev. 89, 863 (1989), incorporated herein by reference. The starting material can also be prepared through a Peterson-Chan olefination reaction, using an $\alpha$-silyl anion.

For example, as shown in Scheme III below, di(protected)oxy-2E-penten-1-ol can be prepared through reaction of ethyl-3,3-di(benzyl)oxypropanoate 9 with diisopropyl Scheme III

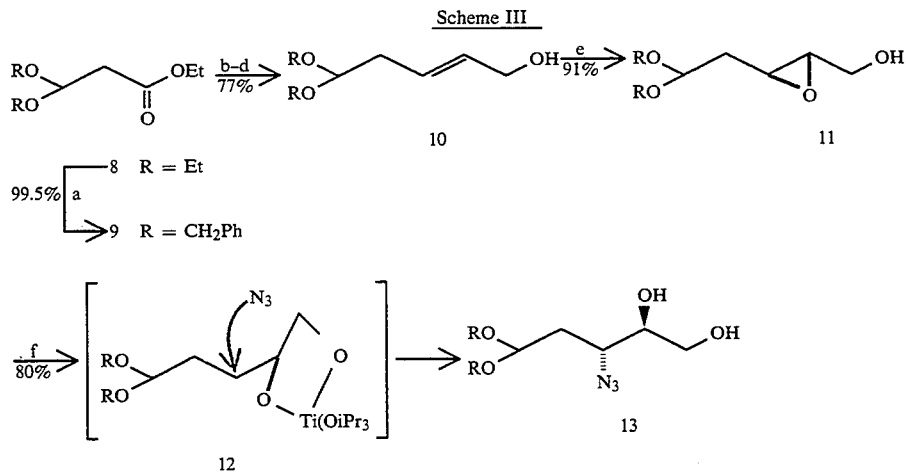

(a) PhCH₂OH, TsOH, benzene, 80° C.; (b) DIBAL-H, Et₂O, −78° C.; (c) (iPrO)₂P(O)CH₂CO₂Et, NaH, THF; (d) 2 equiv. DIBAL-H, Et₂O, −78° C.; (e) Ti(OiPr)₄, (−)-DET, tBuOOH, 4A sieves, CH₂Cl₂, −20° C.; (f) Ti(OiPr)₄, Me₃SiN₃, benzene.

The term "perfluoroalkyl" refers to an alkyl group wherein at least two hydrogens attached to carbon atoms have been replaced with fluorine. Preferred perfluoroalkyl groups include, but are not limited to, $C_1$ to $C_{15}$ straight, branched, or cyclic moieties.

A highly stereoselective process for the preparation of 3'-substituted-2',3'-dideoxynucleosides and 2'-deoxynucleosides by the stereocontrolled cyclization of acyclic, achiral, inexpensive, precursors is presented. The steps involved in the process are outlined in detail below, and then illustrated through working examples for the preparation of 3'-azido-3'-deoxythymidine (AZT) and 3'-fluoro-3'-deoxythymidine (FLT). Compounds referred to in the discussion below are enumerated as shown in the Schemes or Figures.

A. Preparation of 3(S)-substituted-5,5-di(protected)oxy-1,2-(S)-pentanediol i) Preparation of 5,5-di(protected)oxy-2E-penten-1-ol The starting material for this process for the preparation of 3'-substituted-2',3'-dideoxynucleosides and 2'-deoxynucleosides is 5,5-di(protected)oxy-2E-penten-1-ol. It is preferred that oxygen protecting groups in the 5-position of 5,5-di(protected)oxy-2E-penten-1-ol be selected that impart hydrophobicity to the molecule, to aid in later work-up procedures. Suitable protecting groups include benzyl, and other alkyl and acyl derivatives. Other hydrophobic protecting groups are known to those of skill in the art, and are considered within the scope of this disclosure.

The starting material 5,5-di(protected)oxy-2E-penten-1-ol can be made in a number of ways, including by reduction of the product of a Wittig type reaction beethoxycarbonyl methylphosphonate. Ethyl-3,3-di(benzyl)oxypropanoate is easily produced by derivatization of ethyl 3,3-diethoxypropanoate 8, that can be prepared from ethyl vinyl ether and trichloroacetyl chloride in a two step process (see Tietze, L.F.; Voss, E.; Hartfiel, U. Org. Synth., 69, 238 (1990)). It can also be purchased commercially from Aldrich Chemical Company and Fluka Chemie A.G.. Other alkyl-3,3-dialkoxypropanoates useful as starting materials can be prepared using variations of the method of Tietze, et al. The alkyl-3,3-di(protected)oxypropanoate is then reduced to the corresponding aidehyde, 3,3-di(protected)oxypropanal. Reduction can be accomplished in high yield with diisobutylaluminum hydride (DIBAL-H) under anhydrous conditions, or with lithium aluminum hydride, sodium borohydride (although undesirable conjugate additions can also be formed using this reagent), lithium borohydride (LiBH₄), sodium bis(2-methoxyethoxy)-aluminum hydride (Red-Al), or other hydrides or boranes known to those in the art.

In the next step, the aidehyde, 3,3-di(protected)oxypropanal, is converted to the $\alpha,\beta$-unsaturated ester, 5,5-di(protected)oxy-2E-pentanoate, in high yield via the Horner-Emmons modification of the Wittig reaction, using diisopropyl(ethoxycarbonyl) methylphosphonate and sodium hydride in an anhydrous solvent. The Horner-Emmons reaction is highly stereoselective for the desired E-isomer (typically greater than 90%). The reaction is typically performed at a temperature ranging from 25° C. to 67° C. in ether, benzene, or toluene. It is preferred to use approximately one equivalent of diisopropyl (ethoxycarbonyl) methylphosphonate, and approximately one equivalent of sodium hydride or potassium tert-butoxide. Amounts of reagent in excess of this can be used, but result in the need to purify the product. The reaction is usually complete in one to two hours.

5,5-Di(protected)oxy-2E-pentanoate is reduced to the corresponding 5-dibenzyloxy-2E-penten-1-ol with a suitable reducing agent such as diisobutylaluminum hydride (DIBAL-H) under anhydrous conditions, typically in hexane, toluene, benzene, ether, or tetrahydrofuran, preferably at a temperature ranging from −80° C. to −50° C. The reduction can also be accomplished with sodium borohydride, lithium borohydride, sodium bis(2-methoxyethoxy)-aluminum hydride, or lithium aluminum hydride (although this reagent may over reduce the ester), or other hydrides or boranes known to those in the art.

ii) Epoxidation of the 5,5-di(protected)oxy-2E-penten-1-ol to the corresponding 2(S),3(R)-epoxy alcohol In the next step according to this procedure, the prochiral allylic alcohol 5,5-di(protected)oxy-2E-penten-1-ol is converted to the corresponding 2(S),3(R)-epoxy alcohol. In a preferred embodiment, epoxidation is carried out under Sharpless asymmetric epoxidation conditions using D-(−)-dialkyl tartrate (for example, diethyl tartrate, dicyclohexyltartrate, or dicyclododecyl tartrate), titanium tetra(alkoxide), and an organic hydroperoxide such as tert-butyl hydroperoxide or cumene hydroperoxide, in the presence or absence of zeolite molecular sieves, to provide the desired 2(S),3(R) epoxidized product in typically greater than 90% enantiomeric excess (ee). The titanium/tartrate ratio and the temperature of reaction will affect the enantiomeric selectivity of reaction. In general, it is preferred to use at least 20%, and not less than 10%, excess tartrate in generating the titanium/tartrate catalyst. The use of molecular sieves (preferably 3A or 4A) in some cases appears to reduce the amount of titanium catalyst needed for epoxidation, reducing the cost of the final product. It has been observed that generally, however, the more catalyst that is used, the higher the enantiomeric purity, but lower the overall yield. The enantiomeric excess (ee) can be determined by gas chromatographic analysis of the Mosher esters of the epoxy alcohol. The Mosher esters are conveniently formed with (+)-α-methoxy-α-(trifluoromethyl)phenyl-acetyl chloride.

For detailed discussion of the Sharpless asymmetric epoxidation, see: Gao, Y.; Hanson, R.M.; Klunder, J.M.; Ko, S.Y.; Masamune, H.; and Sharpless, K.B., J. Am. Chem. Soc. 109, 5765 (1987), and references cited therein, all incorporated herein by reference.

The penten-1-ol can also be epoxidized with known epoxidizing agents in the absence of the titanium/tartrate catalyst to produce a mixture Of products that can be separated chromatographically. Epoxidation reagents include metachloroperbenzoic acid, peracetic acid, perbenzoic acid, hydrogen peroxide, peroxytrifluoroacetic acid, monoperphthalic acid, and dimethyl dioxirane. Vanadyl acetonyl acetonate (vanadyl (acac)$_2$) can be used as a catalyst.

iii) Addition of nucleophile to the epoxy alcohol to form a 3 (S)-substituted-5,5-di(protected)oxy-1,2(S)-pentanediol.

In the next step, a nucleophile is introduced into the 3-position of the 2(S),3(R)-epoxy alcohol by treating the epoxy alcohol with an appropriate nucleophilic reagent to produce a 3(S)-substituted-5,5-di(protected)oxy-1,2(S)-pentanediol. In a preferred embodiment, Ti(O-alkyl)$_4$, preferably Ti(O-isopropyl)$_4$, is used as a catalyst for the nucleophilic reaction. Caron, M.; Sharpless, K.B., J. Org. Chem., 50, 1557 (1985). The nucleophile is ultimately located in the 3'-position of the target nucleoside.

A nucleophile can be added to the epoxy alcohol by treating the alcohol with a salt or silylated derivative of the desired nucleophile, such as azido (using CH$_3$SiN$_3$ or NAN$_3$), amino, a mono- or di(aliphatic)amine, such as mono- or diethylamine or diallylamine, nitro, chloro (using NH$_4$Cl), cyano (using KCN or CH$_3$SiCN), alkoxy, phenoxy, hydroxy (using, for example, a benzoate or carboxylate such as acetate, that can later be cleaved to the free hydroxyl), alkyl or aromatic mercaptyl, thiophenyl, selenium phenyl, acetylenic, thiocyano (using NH$_4$SCN), allyloxy (using allyl alcohol), bromo (using NH$_4$Br), benzoyl (using NH$_4$OBz or benzoic acid), acetyl (using NH$_4$OAc), alkyl carboxylic acids, LPTS (2,6-lutidine p-toluene sulfonate), and perfluoroalkyl (for example, using perfluoroalkyl cuprate).

The nucleophile is introduced regioselectively by treating the epoxy alcohol with the nucleophile in the presence of Ti(O-alkyl)$_4$, that is thought to coordinate to the epoxide and alcohol to form a bidentate intermediate (Compound 12, Scheme III). In this titanium coordinated complex, the C-3 position of the epoxy alcohol is more reactive toward nucleophilic attack than the C-2. For example, treatment of the epoxy alcohol with Me$_3$SiN$_3$ in the presence of Ti(O-i-Pr)$_4$ yields an azidohydrin with a C-3 to C-2 ratio of 16/1.

The combination of Sharpless epoxidation of the penten-1-ol followed by ring opening of the epoxide and nucleophilic addition in the presence of Ti(alkoxide)$_4$ provides substantial flexibility in controlling the absolute stereochemistry at the two stereogenic centers in the 3(S)-substituted-5,5-di(protected)oxy-1,2(S)-pentanediol. In principle, by varying either the olefin geometry or the absolute configuration of the tartrate, all possible combinations of absolute configurations at these centers are possible.

Addition of Fluoride Anion

Although Ti(O-alkyl)$_4$ substantially improves the stereoselectivity of addition of the nucleophile to the epoxy alcohol, it may not be appropriate for use in the presence of certain nucleophiles, such as fluoride. Further, attempts to open the ring of the 2(S),3(R)-epoxy alcohol using SiF$_4$, anhydrous n-Bu$_4$NF, KHF$_2$-AlF$_3$, or HF-pyridine using published conditions and in the absence of the titanium catalyst results in significant decomposition of the starting epoxy alcohol or no reaction at all.

It has now been discovered that fluorine can be added to the 3-position of the 2(S),3(R)-epoxy alcohol with high regioselectivity by treating the epoxy alcohol with the very mild reagent tetrabutylammonium dihydrogentrifluoride (Bu$_4$NH$_2$F$_3$). Alternatively Bu$_4$PH$_2$F$_3$ can be used. Feto, et al. Chem. Lett. 1991, 1185.

By employing phase transfer conditions, and in particular, solid-liquid phase transfer catalysis with KHF$_2$ and Bu$_4$NH$_2$F$_3$, the 2(S),3(R)-epoxy alcohol can be converted to the corresponding fluorohydrin in good yield, without the use of a titanium reagent. See Landini, D.; Albanese, D.; Penso, M. Tetrahadron Lett. 1992, 48, 4163, for details of the phase transfer conditions, incorporated herein by reference. Briefly, the 2(S),3(R)- epoxy alcohol (an oil) is mixed with Bu$_4$NH$_2$F$_3$ (also an oil) to provide a homogeneous solution. KHF$_2$ is then added to establish the phase transfer conditions. Solvents such as DMF and ethylene glycol dimethylether can be used but they tend to decrease yield.

Any molar ratio of components can be used that provides an adequate yield. As the molar percentage of Bu$_4$NH$_2$F$_3$ increases, a reduction in reaction time and an increase in yield is observed. Typically, between 1 and 2 moles of Bu$_4$NH$_2$F$_3$, and 5–10 moles of KHF$_2$ to one mole of 2(S),3(R)-epoxy alcohol is suitable, but the optimal ratios may change depending on the reaction conditions. Preferred, but not required, molar ratios are approximately 2:10:1 of Bu$_4$NH$_2$F$_3$ to KHF$_2$ to epoxy alcohol. The mixture is heated at any temperature, and for any length of time, that provides an adequate yield. In general, using phase transfer conditions, a reaction time of approximately 3 to 4 hours, and a temperature range of 140°–150° C. provides a good yield of product. It is desireable to carry out the reaction in the atmosphere of an inert gas, including but not limited to argon or nitrogen.

The resulting gum can be worked up by any conventional technique. For example, the gum can be dissolved in ethyl acetate, and washed with sodium bicarbonate. The organic layer is then dried with magnesium sulfate, decolorized with charcoal, filtered, and the solvent removed in vacuo. The resulting material can be purified by any known means, including flash chromatography.

The reaction can also be performed using homogeneous catalysis by eliminating the KHF$_2$ additive while otherwise maintaining the same conditions. Preferred, but not required, conditions for the homogeneous catalysis are: approximately two moles of Bu$_4$NH$_2$F$_3$ to one mole of epoxy alcohol heated for approximately 30 minutes at a temperature of between 140°–150° C. As an example, the Bu$_4$NH$_2$F$_3$ and epoxy alcohol are placed in a round-bottomed flask equipped with a magnetic stir bar and argon inlet. The flask is then immersed in an oil bath and the reaction monitored by thin layer chromatography.

It has also been discovered that by addition of certain protecting groups to the alcohol moiety, the regioselectivity of the hydrofluorination reaction can be improved. It appears that the observed regioselectivity in these Bu$_4$NH$_2$F$_3$-induced hydrofluorinations may be linked to the relative basicity of the non-epoxide oxygen more than its local steric environment. Based on the disclosure herein, one of ordinary skill in the art will easily be able to determine those oxygen protecting groups that are most effective under the selected conditions of reaction.

As shown in Table I, when the alcohol is unprotected, both $^{13}$C NMR and capillary GC analysis indicate that the regioselectivity of the reaction is approximately 5:1 of 1,1-dibenzyloxy-3(S)-fluoro,4-(R)-hydroxyl-5-O-acetylpentane to 1,1-dibenzyloxy-4-fluoro,3-hydroxyl-5-O-acetylpentane. Since the fluorohydrin regioisomers are difficult to separate on a large scale, for certain applications, even higher regioselectivity may be desireable. It was determined that by employing the same reaction conditions and converting the alcohol to the acetate, the regioselectivity for the desired isomer increased to 25:1.

TABLE I

RO-[epoxide]-OBn, OBn  →(1.1–1.5 equiv. Bu$_4$NH$_2$F$_3$)→  RO-CH$_2$-CH(OH)-CHF-CH(OBn)-OBn

| Substrate | Conditions | Yield | Ratio |
|---|---|---|---|
| R = H | 140° C., 12–24h | 72% | 5:1 |
| R = Ac | 150° C., 3–4h | 62% | 25:1 |
| R = BnO | 150° C., 3.5h | 65.5% | 1:1 |
| R = BzO | 150° C., 3h | 71% | 15:1 |

While the regioselectivity of the hydrofluorination reaction using the epoxy acetate is acceptable, the reaction conditions employed result in the hydrolysis of approximately 10% of the acetate, producing the fluorodiol (4:1 regiosomeric ratio) as a by-product.

Under the same reaction conditions, using the 2(S),3(R)-epoxy alcohol wherein the alcohol is protected with a benzyl group, an approximately 1:1 mixture of fluorohydrin regioisomers in a 65.5% yield is recovered. The corresponding benzoate derivative afforded the desired fluorohydrin in 71% yield with a regioisomer ratio of 15:1 and with very little hydrolysis product.

B. Addition of Heterocyclic Base and Cyclization of 3(S)-Substituted-5,5-di(protected)oxy-1,2-(S)-pentanediol A key step in the process for the preparation of 3'-substituted-2',3'-dideoxynucleosides and 2'-deoxynucleosides is the stereoselective kinetically controlled cyclization of the pentanediol under protic or Lewis acid conditions. The 3'-substituted-2',3'-dideoxynucleosides or 2'-deoxynucleosides are obtained by either: (1) addition of the heterocyclic base to the pentanediol to form an aminal compound, followed by cyclization of the aminal, or (2) cyclization of the pentanediol acetal to a derivatized ribose followed by addition of the heterocyclic base. The former route is preferred because it avoids the formation of a significant amount of undesired α-anomeric nucleoside. The latter scheme provides a mixture of α and β-anomeric nucleosides that can be separated under known conditions to provide the biologically active β-anomeric nucleoside. The cyclization reaction is typically performed at a temperature of between −20° C. and 25° C. (−5° C. to −20° C. for the acetal, 25° C. for the aminal). The aminal cyclization is preferably performed in tetrahydrofuran, methanol, ethanol, or isopropyl alcohol. The acetal cyclization is preferably performed in methylene chloride or tetrahydrofuran.

i) Addition of Heterocyclic Base to 3(S)-Substituted-5,5-di(protected)oxy-1,2 (S)-pentanediol In a preferred embodiment, the heterocyclic base is substituted for one of the benzyloxy groups in the 5-position of (S)-substituted-5,5-di(protected)oxy-1,2(S)-pentanediol 13. Under Vorbruggen coupling conditions, an approximate 1/1 mixture of aminal diastereomers is produced. However, this does not adversely affect the stereoselectivity of the overall reaction because both diastereomers apparently cyclize via the same iminium ion intermediate, illustrated below in Scheme IV.

Scheme IV

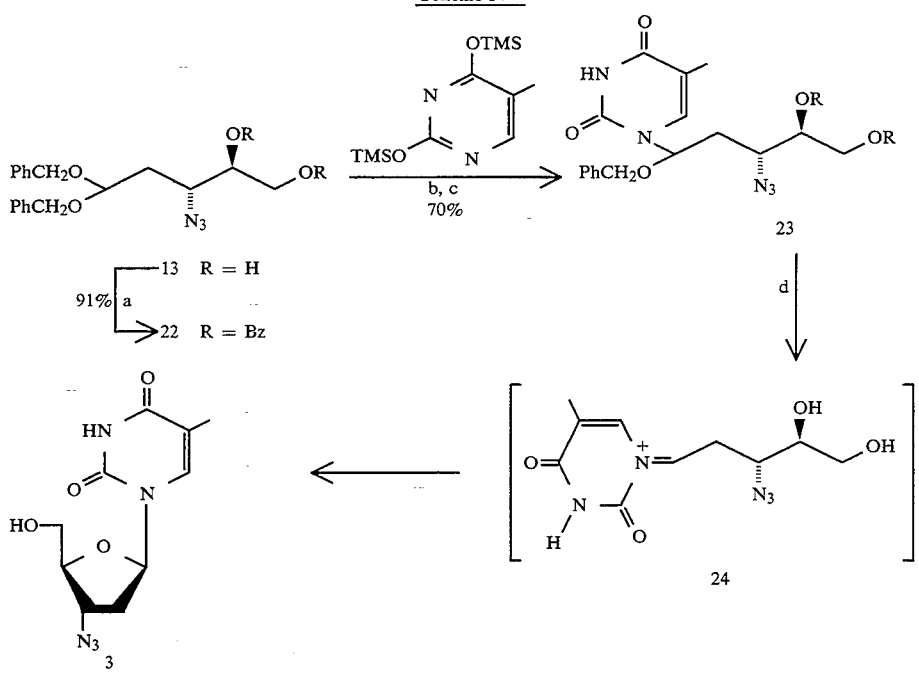

(a) 2.2 equiv. PhCOCl, NEt₃, DMAP, CH₂Cl₂; (b) 1.5 equiv. (CH₃)₃SiOTf, ClCH₂CH₂Cl;
(c) 2 equiv. NaOH, MeOH; (d) 0.1M Soln. 1:3 H₂SO₄:THF, 0–25° C., 1.5 d.

Before adding the heterocycle to the pentanediol, the 1,2-dihydroxyl groups should be protected to form a 3(S)-substituted-5,5-(diprotected)oxy-1,2(S)-pentane-(protected diol) 22. Suitable hydroxy protecting groups are known to those skilled in the art, and include benzoyl, trityl, acyl groups such as acetyl, propionyl, p-NO₂ benzoyl, or toluyl, methylsulfonyl, p-toluylsulfonyl, and other organooxysulfonyl groups, silyl (that can be easily removed with tetrabutylammonium fluoride), trisubstituted silyl groups including trimethylsilyl, dimethylhexylsilyl, t-butyldimethylsilyl, t-butyldiphenylsilyl, and alkyl carbonates, such as N-(tert-butoxycarbonyl) derivatives (BOC derivatives).

Any heterocyclic compound, preferably a purine or pyrimidine, containing a nitrogen that is capable of reaction with a center of electron deficiency can be reacted with the 3(S)-substituted-5,5-di(protected)oxy-1,2(S)-pentane-(protected diol) in the base/pentanediol condensation reaction to produce a 5-(protected)oxy-5-(heterocyclic base)-3(S)-substituted-1,2(S)-pentanediol. Purine bases include adenine, hypoxanthine, guanine, N⁶-alkylpurines, N⁶-benzylpurine, N⁶-halopurine, N⁶-vinylpurine, N⁶-acetylenic purine, N⁶-acyl purine, N⁶-hydroxyalkyl purine, and N⁶-thioalkyl purine. Pyrimidine bases include thymine, cytosine, 6-azapyrimidine, 2-mercaptopyrmidine, uracil, N⁵-alkylpyrimidines, N⁵-benzylpyrimidines, N⁵-halopyrimidines, N⁵-vinylpyrimidine, N⁵-acetylenic pyrimidine, N⁵-acyl pyrimidine, N⁵-hydroxyalkyl purine, and N⁶-thioalkyl purine. Functional oxygen and nitrogen groups on the heterocyclic base should be protected before condensation with the pentanediol. Protecting groups are well known to those skilled in the art, and include trimethylsilyl, dimethylhexylsilyl, t-butyldimethylsilyl, t-butyldiphenylsilyl, tritylmethyl, alkyl groups, acyl groups such as acetyl and propionyl, and methylsulfonyl and p-toluenesulfonyl.

The condensation reaction can be carried out under protic or Lewis acid conditions. Suitable protic acids for the sulfuric acid, hydrochloric acid, and halogenated acetic acids, such as trifluoroacetic acid.

Friedel-Crafts catalysts (Lewis acids) that can be used in the condensation reaction include SnCl₄, ZnCl₄, TiCl₄, AlCl₃, FeCl₃, BF₃-diethyl ether, BCl₃, ROTiCl₃, (RO)₂TiCl₂, and (RO)₃TiCl, wherein R is an alkyl group, preferably a C₁ to C₁₀ straight or branched group. These catalysts require anhydrous conditions because the presence of water reduces their activity. The catalysts are also inactivated in the presence of organic solvents with active hydrogens, such as alcohols and organic acids. The catalysts are typically used in solvents such as carbon disulfide, methylene chloride, nitromethane, 1,2-dichloroethane, nitrobenzene, tetrachloroethane, chlorobenzene, benzene, toluene, dimethylformamide, tetrahydrofuran, dioxane, or acetonitrile. Niedballa, et al., *J. Org. Chem.* 39, 25 (1974).

Trimethylsilyl triflate ((CH₃)₃SiOSO₂CF₃), (CH₃)₃SiOSO₂C₄F₉, and (CH₃)₃SiClO₄ can be used under the same conditions described above for the Friedel-Crafts catalysts. Vorbruggen, H.; Krolikiewicz, K.; Bennua, *B. Chem. Bet.*, 114, 1234 (1981). The amount of the triflate used in general depends on the temperature and time of reaction; for example, approximately one equivalent of triflate is suitable when used at 25° C. for 24 hours, 1.5 equivalents when used at 25° C. for 8 hours, and 0.2 equivalents when used at 80° C. for 24 hours. These strong acidic conditions may cleave acetate protecting groups.

After condensation, the heterocyclic protecting groups and the 1,2-dihydroxy protecting groups can be removed by treating the product with a stoichiometric amount of a base such as sodium methoxide. Under acidic conditions, the acyl protecting groups are removed but some cyclization can also take place. Silyl groups can be removed with fluoride ion.

ii) Cyclization of 5-(protected)oxy-5-(heterocyclic base)-3(S)-substituted-1,2(S)-pentanediol and deprotection to form 3'-substituted-2',3'-dideoxynucleoside In the final step, in a preferred embodiment, the 5-(protected)oxy-5-(heterocyclic base)-3(S)-substituted-1,2(S)pentanediol is stereoselectively cyclized and then deprotected to form a 3'-substituted-2',3'-dideoxynucleoside Cyclization of 5-(protected)oxy-5-(heterocyclic base)-3(S)-substituted-1,2(S)-pentanediol can be carried out in moderately concentrated acidic conditions. Suitable protic acids include sulfuric acid (10 fold excess) or perchloric acid (10 fold excess) dissolved in 9.5 N sulfuric acid in methanol. Many other suitable protic acids are known to those skilled in the art and are considered within the scope of this invention. The reaction is preferably performed at approximately 25° C. in methanol, ethanol, isopropyl alcohol, or tetrahydrofuran.

For example,5-benzyloxy-5-thymine-3(S)-azido-1,2(S)-pentanediol 23 can be cyclized in a 0.1M solution of ⅓ $H_2SO_4$ in THF to give exclusively the β-anomer of AZT in a 25% yield with recovery of 65% starting material (72% yield based on recovered starting material, see Scheme IV).

iii) Stereochemical Control of Cyclization

The thermodynamic and kinetic stereoselectivity of cyclization of the pentanediol was investigated on model compound 3(S)-substituted-5,5-di(protected)oxy-1,2(S)-pentanediol 13 as a function of acid, using the following procedure. The results are provided in Table 31.

Thermodynamic Conditions with $H_2SO_4$ To a 25 mL round-bottomed flask (purged with argon) was added 3(S)-azido-5-dibenzyloxy-1,2(S)-pentanediol (13, 374 mg, 0.00105 mole) and tetrahydrofuran ("THF," 7.0 mL). The solution was stirred at ambient temperature, and then $H_2SO_4$ (0.210 mL, 1N solution in THF) was added. The mixture was allowed to stir for 3 hours at ambient temperature, and was then diluted with $CH_3OH$ (10 mL), cooled to 0° C. and neutralized with sodium bicarbonate. The mixture was then filtered and solvent removed in vacuo. The resulting residue was purified by flash chromatography (α-anomer 15: $R_f$=0.68, β-anomer 16: $R_f$=0.41) to give 15 (23% yield) and 16 (48% yield) colorless oils.

Kinetic Conditions with $H_2SO_4$. To a 25 mL three necked round-bottomed flask equipped with a magnetic stir bar, thermometer inlet with thermometer, septum, and argon inlet was added 3(S)-azido-5-dibenzyloxy-1,2(S)-pentanediol (13, 230 mg, 0.6440 mmole) and THF (5 mL). The solution was cooled to −5° C. under argon and $H_2SO_4$ (1.9 ml, 1N in THF) was added dropwise while maintaining a reaction temperature of 0° C. to −5° C. The mixture was stirred for 0.5 hours at 0° C. Dilution with cooled (0° C.) $CH_3OH$ (10 mL) was followed by addition of sodium bicarbonate to neutralize the acidic mixture. The mixture was filtered and solvent removed in vacuo. The resulting residue was purified by flash chromatography to give 3-azido-1-β-benzyloxy-4-hydroxylmethyltetrahydrofuran (16, 118 mg, 74% yield) as a colorless oil.

Thermodynamic Conditions with p-TsOH. To a 25 mL round-bottomed flask was added 3 (S)-azido-5-dibenzyloxy-1, 2(S)-pentanediol (13, 500 mg, 1.399 mmole) and THF (10 mL). To the cooled (0° C.) solution was added p-toluenesulfonic acid monohydrate (266 mg, 1.399 mmole) and the mixture was stirred for @12 h with gradual warming to ambient temperature. The mixture was diluted with $CH_3OH$ (25 mL) and neutralized with $NaHCO_3$. The mixture was filtered and solvent removed in vacuo. The resulting residue was purified by flash chromatography to give 15 (108 mg, 31% yield) and 16 (55.8 mg, 16%) as colorless oils.

Thermodynamic Conditions with Lewis Acid. To a 25 mL round-bottomed flask was added 3(S)-azido-5-dibenzyloxy-1, 2(S)-pentanediol (13, 184 mg, 0.52 mmole) and dichloroethane (5 mL). The solution was stirred at ambient temperature and then $(CH_3)_2SiCl_2$ (100 mg, 0.78 mmole) was added. The mixture was stirred at ambient temperature for another 2.5 hours. The mixture was diluted with ether:hexane (2:1, 20 mL) and then poured through a short plug of silica gel. The solvent was removed in vacuo to give 15 (62 mg, 48% yield) and 16 (42 mg, 32% yield) as colorless oils.

Kinetic Conditions with Lewis Acid. To a 25 mL three necked round-bottomed flask equipped with a magnetic stir bar, a thermometer inlet. with thermometer, septum, and argon inlet was added 3(S)-azido-5-dibenzyloxy-1,2(S)-pentanediol (13, 790 mg, 2.21 mmole) and $CH_2Cl_2$ (11.4 mL). The solution was cooled to −5° C. under an argon atmosphere and $SiCl_4$ (3.3 mL of a 1M solution in $CH_2Cl_2$) was added dropwise maintaining a reaction temperature of 0° C. The mixture was stirred for 0.5 hour at 0° C. and quenched with wet ether:hexane (2:1, 50 mL). The mixture was poured through a short plug of silica gel to give 16 (424 mg, 77% yield) as a colorless oil.

3-azido-1αa-benzyloxy-4-hydroxymethylhydrotetrafuran (15). $^1$H NMR (CDCl$_3$) d 2.13–2.22 (m, 1H), 2.32–2.44 (m, 2H), 3.58–3.66 (m, 1H), 3.78 (dr, 1H, J=3.2 Hz, Dn=12.1 Hz), 4.10 (q, 1H, J=3.7 Hz), 4.25 (m, 1H), 4.55 (d, 1H, J=11.7 Hz), 4.76 (d, 1H, J=11.7 Hz), 5.32 (dd, 1H, J=1 Hz, Dn=5.2 Hz), 7.29–7.36 (m, 5H); $^{13}$C NMR (CDCl$_3$) d 39.39, 60.69, 63.54, 70.04, 85.09, 103.26, 127.97, 128.02, 128.57, 137.06; IR (Neat) 3705–3165 (broad), 3100, 3085, 3050, 2935, 2885, 2110 (N$_3$), 1500, 1455, 1400, 1360, 1330, 1255, 1215, 1180, 1095, 1030, 945, 915, 740, 700; LRFAB 256 (M+Li)$^+$, 160 (100), 126 (20); HRFABMS calcd for $C_{12}H_{15}N_3O_3Li$ (M+Li)+256.1273, found 256.1274.

3-Azido-1β-benzyloxy-4-hydroxymethyltetrahydrofuran (16). $^1$H NMR (CDCl$_3$) d 2.12 (ddd, 1H, J=1.5 Hz, 3.9 Hz, 14.1 Hz), 2.41 (m, 1H), 3.67 (d, 1H, J=12.4 Hz), 3.85 (dd, 1H, J=2.8 Hz, 12.4 Hz), 3.95 (m, 1H), 4.05 (m, 1H), 4.50 (d, 1H, J=12.1 Hz), 4.76 (d, 1H, J=12.1 Hz), 5.25 (dd, 1H, J=1.1 Hz, 5.2 Hz), 7.33 (m, 5H); $^{13}$C NMR d 38.82, 59.54, 61.90, 68.99, 82.32, 102.32, 127.55, 127.67, 128.28, 128.34, 137.51; IR (Neat) 3700–3200 (broad), 3110, 3085, 3050, 2945, 2895, 2110 (N$_3$), 1610, 1510, 1460, 1370–1340 (broad), 1315, 1265, 1220, 1200, 1115, 1075, 1045, 920, 740, 700; LRFAB 256 (M+Li)+160 (100), 126 (50); HRFABMS calcd for $C_{12}H_{15}N_3O_3Li$ (M+Li)+256. 1273, found 256.1277.

TABLE II

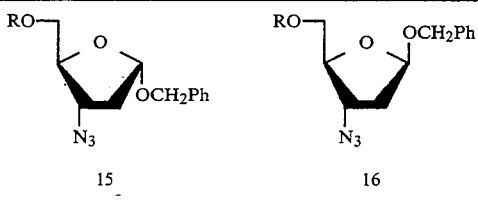

| CONDITIONS | 16:15 | YIELD |
|---|---|---|
| p-TsOH, 80° C. | 1:1 | 15% |
| p-TsOH, 0°–25° C. | 1:2 | 47% |
| 0.1xH$_2$SO$_4$, 25° C. | 1:2 | 71% |
| 1.5xH$_2$SO$_4$, −5° C. | >95:5 | 74%[a] |
| 1.5x(CH$_3$)$_2$SiCl$_2$, 25° C. | 1:1.5 | 81%[b] |
| 1.5x(CH$_3$)$_2$SiCl$_2$, 0° C. | >95:5 | 79%[a,b] |
| 1.5xSiCl$_4$, 0° C. | >95:5 | 77%[a] |

[a]Using 300 MHz $^1$H NMR results, no a-anomer is observed.
[b]No silylated products are observed in the crude reaction mixture.

It appears that 3(S)-substituted-5,5-di(protected)oxy-1,2(S)-pentanediol 13 cyclizes to the carbohydrate derivatives 15 and 16 under acidic conditions via an oxonium intermediate.

As indicated in Table II, only one product, the β-anomer, is observed under kinetic conditions (−5° C.) using either a protic acid or mild Lewis acid conditions during the cyclization of 3(S)-substituted-5,5-di(protected)oxy-1,2(S)-pentanediol. To secure the fact that the other product formed under thermodynamic conditions (25° C.) is actually a 5-member ring rather than a 6-member ring carbohydrate, the primary hydroxyl group of 13 was protected as a benzoate and exposed to the same acidic conditions. The two products observed from this cyclization exhibit the same spectral and chromatographic properties as the benzoates (20,21) of the carbohydrate derivatives 15 and 16.

Stereochemical Control in the Formation of 1-(5-O-Acetyl-3-fluoro-2,3-dideoxy-β-D-erythro-pentofuranosyl)thymine and and 1-(5-O-acetyl-3-fluoro-2,3-dideoxy-α-D-erythro-pentofuranosyl)thymine.

When exposed to Vorbruggen conditions (2 equiv. bis-O-trimethylsilylthymine, 2 equiv. TMSOTf, CH$_3$CN, 2.75h), the fluorohydrin was converted to FiT acetate in 71% yield (2.8:1, β:α), as shown below.

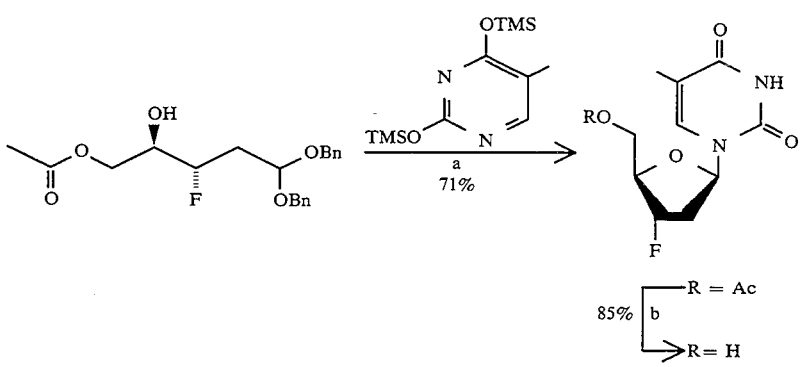

(a) 2 equiv. TMSOTf, CH$_3$CN, 25° C., 2.8:1 β:α;
(b) NaOMe, MeOH.

Removal of the acetate moiety with NaOMe/MeOH provided FLT, in high yield (approximately 85%). When the reaction was performed under identical conditions but stopped after fifteen minutes, no starting material remained. Instead, the reaction mixture consisted almost exclusively of the cyclized compound. Thus, unlike its azido counterpart, the cyclization of 33 to FLT appears to be much faster than the aminal exchange of 33 to 35.

iv) Preparation of 3'-substituted-2',3'-dideoxynucleosides from 3-(substituted)-1-(α or β) (protected) oxy-4-hydroxymethyltetrahydrofuran (15)

In an alternative embodiment, as shown in Scheme V, 3-(substituted)-1-(α or β)-protected oxy-4-hydroxymethyltetrahydrofuran can be condensed with a heterocyclic base under similar conditions to those discussed in Section B. iii) above to form a mixture of α and β anomeric 3'-substituted-2',3'-dideoxynucleosides. Even though the final step in the above synthesis results in an undesirable mixture of α and β-anomers of AZT, this cyclization strategy can be used to prepare β-nucleosides.

As an example, the benzoates 20 and 21 were separately treated with silylated thymine in the presence of TiCl$_4$ to yield a mixture of α and βd-anomers of AZT benzoates (see Scheme VI). The benzoate groups are easily removed by sodium methoxide to afford AZT in a 2/1 (α/β) ratio from 20 and a 1/1 ratio from 21.

Scheme V

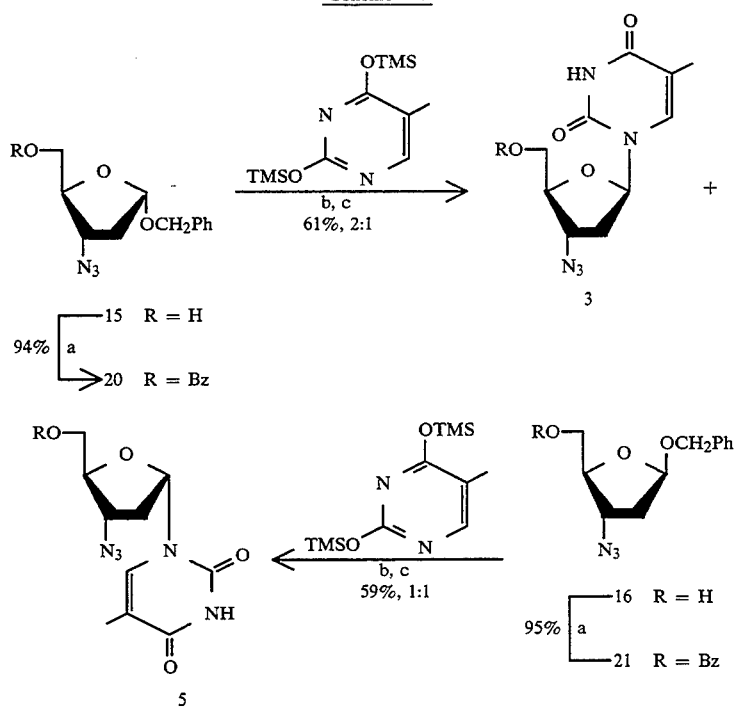

(a) PhCOCl, NEt₃, DMAP, CH₂Cl₂; (b) TiCl₄, ClCH₂CH₂Cl; (c) NaOH, MeOH.

Example 1 Detailed example for the preparation of 3'-azido-3'-dideoxythymidine

Reactions were performed under a positive pressure of dry nitrogen or argon. Solvents and reagents were purchased from Aldrich Chemical Co. and Fluka Chemical Co. Solvents were purified and dried according to. Perrin, D.D. and Armarego, W.L.F. Purification of Laboratory. Chemicals; 3rd Edition; Pergamon Press: New York, 1988. Flash chromatography employed E. Merck Silica Gel (Kieselgel 60, 230–400 mesh). Preparative thin layer chromatography was performed with 0.5 mm precoated silica gel plates (E. Merck, DC-Fertigplatten, Kieselgel F-254) and analytical thin layer chromatography was performed with precoated silica gel plates (E. Merck, DC-Fertigplatten, Kieselgel 60 F-254). GC analysis was performed on Hewlett Packard 5880A gas chromatograph equipped with SPB-5 on fused silica column. Melting points were obtained on a Thomas-Hoover apparatus in open capillary tubes and are uncorrected. Optical rotations were taken on a Perkin Elmer Model 241MC Polarimeter.

Proton nuclear magnetic resonance ($^1$H NMR) and carbon nuclear magnetic resonance ($^{13}$C NMR) were recorded on QE-300 (300.1MHz and 75 MHz respectively) instrument that was funded through NSF Grant CHE-8516614. Infrared (IR) spectra were recorded on a Perkin-Elmer 1430 ratio recording infrared spectrophotometer. Low resolution fast atom bombardment mass spectra were obtained from a VG 70-S mass-spectrometer (funded through NIH S10-RR-02478). High resolution fast atom bombardment mass spectra were obtained from Midwest Center for Mass Spectrometry at the University of Nebraska-Lincoln. Microanalysis were performed by Atlantic Microlab, Inc. (Norcross, Georgia).

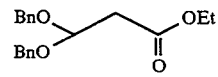

Ethyl 3,3-dibenzyloxypropionate (9). To a 1000 mL round-bottomed flask was added ethyl 3,3-diethoxypropionate (20.0 g, 0.1051 mole), benzyl alcohol (22.7 g, 0.2102 mole), p-toluenesulfonic acid monohydrate (0.5 g, 0.0026 mole) and benzene (800 mL). The reaction can also be carried out in hexanes Heating the mixture at 80° C., the solvent was distilled from the reaction mixture in a 3.5 hour period monitored by 300 MHz NMR. The reaction can be carried out in hexanes. The resulting residue was dissolved in ether (@300 mL) and washed with saturated sodium bicarbonate solution (100 mL) and brine (100 mL). The organic layer was dried over anhydrous magnesium sulfate and the solvent removed in vacuo to give ethyl 3,3-dibenzyloxypropionate (9) as a colorless oil (32.9 g, 99.5% yield): $^1$H NMR (CDCl₃) d 1.22 (t, 3H, J=7.2 Hz), 2.79 (d, 2H, J =5.9 Hz), 4.12 (q, 2H, J=7.2 Hz), 4.60 (d, 2H, J=11.6 Hz), 4.70 (d, 2H, J=11.6 Hz), 5.22 (t, 1H, J=6 Hz), 7.27–7.36 (m, 10H); IR (Neat) 3100, 3080, 3040, 2990, 2940, 2920, 2885, 1740, 1630, 1458, 1375, 1315, 1190, 1120, 1050, 1030, 740, 700.

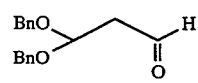

3,3-Dibenzyloxypropanal. To a 1000 mL round-bottomed flask was added ethyl 3,3-dibenzyloxypropionate (9, 15 g, 0.0477 mole) and ether (300 mL). The solution was cooled to −78° C. under a dry argon atmosphere and diisobutylaluminum hydride (47.7 mL of 1M solution in hexanes, 0.0477 mole) was added dropwise. The mixture was stirred for 0.5 h at −78° C. followed by quench with methanol (20 mL). The mixture was allowed to warm to 0° C. and washed 2 times with potassium sodium tartrate, tetrahydrate 20% solution in water (2@250 mL), brine (200 mL) and then dried over anhydrous magnesium sulfate. The solvent was removed in vacuo to give 3,3-dibenzyloxypropanal as a colorless oil (12.1 g, 94% yield): $^1$H NMR d 2.83 (dd, 2H, J=2, 5.3 Hz), 4.61 (d, 2H, J =11.6 Hz), 4.69 (d, 2H, J=11.6 Hz), 5.20 ( t, 1H, J=5.5 Hz), 7.27–7.36 (m, 10H), 9.74 (s, 1H); IR (Neat) 3100, 3080, 3045, 2940, 2895, 1735, 1500, 1460, 1390, 1360, 1210, 1110, 1060, 1030, 740, 700.

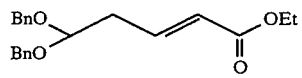

5,5-Dibenzyloxy-2E-pentenoate. To a 1000 mL round-bottomed flask was added NaH (1.07 g, 0.0448 mole) and anhydrous THF (350 mL). The suspension was cooled to 0° C. under a dry argon atmosphere. To the suspension was added dropwise diisopropyl (ethoxycarbonyl methyl) phosphonate (11.3 g, 0.0448 mole). The mixture was allowed to warm to ambient temperature and stirred for 0.5 hour. Then 3,3-dibenzyloxypropanal (12.1 g, 0.0448 mole) was added and stirred for 5 hours at ambient temperature.The reaction was quenched with saturated ammonium chloride solution (100 mL) and the THF was removed in vacuo. The resulting orange residue was dissolved in ether (300 mL). The organic layer was washed 3 times with water (3@100 mL) and dried over anhydrous magnesium sulfate. The solvent was removed in vacuo . The resulting orange oil was purified flash chromatography (Rf=0.29, 14.3% EtOAc in hexanes) to give 5-dibenzyloxy-2-pentenoate as a colorless oil (12 g, 90% yield). A ratio of 98:2 (cis:trans) was determined by GC analysis (SPB-5 on fused silica): $^1$H NMR (CDCl$_3$) d 1.27 (t, 3H, J=7.1Hz), 2.64 (t, 2H, J=6.08 Hz), 4.17 (q, 2H, J=7.1Hz), 4.54 (d, 2H, J=11.7 Hz), 4.64 (d, 2H, J=11.7 Hz), 4.82 (t, 1H, J=5.6 Hz), 5.86 (d, 1H, J=15.9 Hz), 6.98–6.88 (m, 1H), 7.28–7.36 (m, 10H); $^{13}$C NMR (CDCl$_3$) d 14.02, 36.46, 60.01, 67.46, 100.22, 123.79, 127.53, 128.22, 137.48, 142.75, 165.95; IR (Neat) 3080, 3045, 3000, 2950, 2920, 2890, 1730, 1665, 1500, 1458, 1330, 1270, 1220, 1180, 1110, 1040, 740, 700; LRFAB: 347 (M+Li)+, 222 (4), 181 (9), 91 (100).

Anal. Calcd for C$_{21}$H$_{24}$O$_4$: C, 74.09; H, 7.11. Found: C, 73.98; H, 7.14.

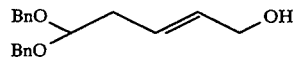

5,5-Dibenzyloxy-2E-penten-1-ol (10). To a 1000 mL round-bottomed flask was added 5-dibenzyloxy-2-pentenoate (12 g, 0.0353 mole) and ether (300 mL). The solution was cooled to −78° C. under dry argon atmosphere and diisobutylaluminum hydride (74.1 mL of 1M solution in hexanes, 0.0741 mole) was added. The mixture was stirred for 0.5 h at −78° C. followed by a quench with methanol (40 mL). The mixture was allowed to warm to 0° C. and washed 3 times with potassium sodium tartrate, tetrahydrate 20% solution in water (3@300 mL) and brine (200 mL). The organic layer was dried over anhydrous magnesium sulfate and the solvent was removed in vacuo. The resulting residue was purified by flash chromatography (Rf=0.57, 50% EtOAc in hexanes) to give 5-dibenzyloxy-2-penten-1-ol (10) as a colorless oil (9.79 g, 93% yield): $^1$H NMR d 1.25 (broad s, 1H), 2.52 (t, 2H, J=5.45 Hz), 4.07 (broad s, 2H), 4.54 (d, 2H, J=11.7 Hz), 4.65 (d, 2H, J=11.7 Hz), 4.75 (t, 1H, J=5.7 Hz), 5.76–5.64 (m, 2H), 7.36–7.28 (m, 10H); $^{13}$C NMR (CDCl$_3$) d 36.02, 62.69, 66.93, 101.01, 125.95, 127.13, 127.18, 127.26, 127.88, 127.94, 131.86, 137.44; IR (Neat) 3700–3200 (broad), 3100, 3090, 3040, 2930, 2890, 1610, 1505, 1460, 1390, 1355, 1210, 1130, 1090, 1025, 740, 700; LRFAB: 305 (M+Li)+ 160 (20), 91 (100)

Anal. Calcd for C$_{19}$H$_{22}$O$_3$: C, 76.48; H, 7.43. Found: C, 76.28; H, 7.45.

Epoxy Alcohol (11). To a 1000mL three necked round-bottomed flask (flame dried) equipped with a magnetic stir bar, a thermometer inlet with thermometer, septum, and argon inlet was added 5-dibenzyloxy-2-penten-1-ol (10, 9.0 g, 0.0302 mole), 10 g of 4A powdered,activated molecular sieves and dry CH$_2$Cl$_2$ (250 mL). The solution was cooled to −10° C. under a dry argon atmosphere and D-(−)-Diethyl Tartrate (0.74 g, 3.62 mole) and Ti(O-i-Pr)$_4$ (0.86 g, 3.02 mmole) were added sequentially. The mixture was stirred at −10° C. for 0.5 h and tert-butyl hydroperoxide (15.1 mL of a 3.0M solution in 2,2,4-trimethylpentane, 0.0453 mole) was added dropwise (over@15 min). The mixture was stirred for 6 h at −5° C. The mixture was poured into an aqueous solution of ferrous sulfate heptahydrate (13.9 g, 0.05 mole) and citric acid (9.6 g, 0.05 mole) in deionized water (50 mL) at 0° C. The two-phased mixture was stirred for 15 min and then transferred to a separatory funnel. The phases were separated and the aqueous phase was extracted 3 times with ether (3@75 mL). The organic layers were combined and treated with a precooled (0° C.) solution of 30% NaOH (w/v) in saturated brine (6 mL). The two-phased mixture was stirred for 45 min at 0° C. and transferred to a separatory funnel. After dilution with water (30 mL) the phases were separated and the aqueous phase extracted 3 times with ether (3@50 mL). The organic layers were combined and dried over anhydrous magnesium sulfate. The solvent was removed in vacuo and the resulting residue was purified by flash chromatograPhY (Rf=0.32, 50% EtOAc in hexanes) to give the epoxy alcohol 11 as a colorless oil (8.6 g, 91% yield, 96% ee by GC analysis of the Mosher Ester): [a]$^{25}$D $^{20.40}$ (c 1.5, CH$_3$OH); $^1$H NMR (CDCl$_3$) d 1.91–2.08 (m, 2H), 2.94 (m, 1H), 3.08 (m, 1H), 3.58 (m, 1H), 3.86 (d, 1H, J=11.8 Hz), 4.57 (dd, 2H, J=6.41 Hz, 11.6 Hz), 4.69 (d, 2H, J=11.6 Hz), 4.93 (dd, 1H, J=1.3 Hz, 5.0 Hz), 7.27–7.43 (m, 10H); NMR.(CDCl$_3$) d 35.61, 51.81, 57.85, 61.12, 67.01, 67.62, 99.41, 127.22, 127.25, 127.92, 137.28; IR (Neat) 3700–3200 (broad), 3100, 3090, 3040, 2940, 2890, 1610, 1500, 1460, 1390, 1360, 1230, 1130, 1050, 1025, 915, 885, 740, 700; LRFAB: 321 (M+Li)+, 99 (100); 297 (M+H-H$_2$O)+, 99 (100), 77 (5).

Anal. Calcd for C$_{19}$H$_{22}$O$_4$: C, 72.59; H, 7.05. Found: C, 72.59; H, 7.02.

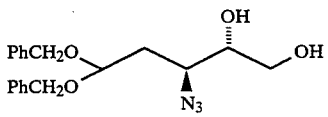

3(S)-Azido-5-dibenzylethy-1,2(S)-pentanediol (13).

A 500 mL airless flask (flame dried), fitted with a condenser and a rubber septum, was evacuated and backfilled with argon 2 times. To the flask was added Ti(O-i-Pr)$_4$ (19.4 g, 0.068 mole), (CH$_3$)$_3$SiN$_3$ (4.7 g, 0.041 mole) and benzene (200 mL) and the mixture was heated under reflux for 5 h. The yellow mixture was then cooled to 0° C. and the epoxy alcohol 11 was added under an argon flush. The resulting orange mixture was stirred at 0° C. for @3.5 h (monitored by TLC). The mixture was diluted with ether (300 mL) and washed 2 times with cooled (0° C.) 5% HCl solution (2 @400 mL) and brine (100 mL). The organic layer was dried with anhydrous sodium sulfate and solvent removed in vacuo. The residue was purified by flash chromatography (Rf=0.26, 50% EtOAc in hexanes) to give the azido hydrin 13 as a colorless oil (7.8 g, 80% yield). A ratio of 16:1 (C-3:C-2 epoxide opening) was determined by $^1$H NMR (300.1MHz) of the diacetate of 13: $^1$H NMR (CDCl$_3$) d 1.86–1.95 (m, 1H), 2.06–2.14 (m, 2H), 2.89 (s, 1H), 3.60–3.69 (m, 4H), 4.55 (d, 2H, J=11.6 Hz), 4.70 (dd, 2H, J=4.4, 11.6 Hz), 4.94 (dd, 1H, J=2.0, 6.5 Hz), 7.28–7.38 (m, 10H); $^{13}$C NMR (CDCl$_3$) d 34.50, 60.37, 62.98, 68.18, 68.25, 73.49, 99.67, 127.83, 127.87, 127.92, 128.48, 137.41; IR (Neat) 3700–3200 (broad), 3100, 3090, 2940, 2890, 2120 (N$_3$), 1610, 1500, 1458, 1395, 1355, 1265, 1210, 1130, 1050, 1025, 740, 700; LRFAB: 364 (M+Li)$^+$, 313 (28), 160 (100), 136 (17).

Anal. Calcd for C$_{19}$H$_{23}$N$_3$O$_4$: C, 63.85; H, 6.49; N, 11.76. Found: C, 63.93; H, 6.54; N, 11.66.

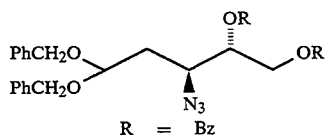

R = Bz

3(S)-Azido-5-dibenzyloxy-1,2(S)-pentanedibenzoate (22).

To a 100 mL round-bottomed flask was added 3 (S)-Azido-5-dibenzyloxy-1,2(S)-pentanediol (13, 1.0 g, 0.0028 mole), triethylamine (1.0 g, 0.0098 mole), 4-dimethylaminopyridine (17 mg, 0.1400 mmole), and CH$_2$Cl$_2$ (50 mL). The mixture was cooled to 0° C. under a dry argon atmosphere and benzoyl chloride (0.85 g, 0.0060 mole) was added dropwise (over ca. 5 min). The mixture allowed to warm slowly to ambient temperature and was stirred for 12 h at ambient temperature. The solvent was removed in vacuo and the resulting residue was dissolved in ether (100 mL). The organic layer was washed 2 times with saturated hydroxylamine sulfate solution (2@50 mL), 2 times with water (2@50 mL), 2 times with 5% HCl solution (2@50 mL) and dried over anhydrous magnesium sulfate. The organic layer was diluted with hexanes (100 mL) and poured through a plug of silica gel. The solvent was removed in vacuo to give 3 (S)-Azido-5-dibenzyloxy-1,2(S)-pentanedibenzoate (22, 1.4 g, 91% yield) as a colorless oil: $^1$H NMR (CDCl$_3$) d 1.90–1.99 (m, 1H), 2.10–2.18 (m, 1H), 4.03 (dr, 1H, J=4.1Hz, 10.9 Hz), 4.54–4.73 (m, 6H), 4.96 (dd, 1H, J=4.3 Hz, 7.7 Hz), 5.53 (dr, 1H, J=4.4 Hz, 6.3 Hz), 7.30–7.57 (m, 16H), 8.00 (dd, 2H, J=7.5 Hz, 21.6 Hz); 13C (CDCl$_3$) d 34.93, 59.80, 62.65, 68.22, 68.24, 73.61, 99.57, 127.80, 127.88, 127.97, 128.45, 128.54, 129.64, 129.70, 129.78; IR (Neat) 3080, 3020, 2940, 2875, 2110 (N$_3$), 1725, 1605, 1590, 1500, 1450, 1355, 1315, 1260, 1100, 1065, 1020, 740, 700; LRFAB: 572 (M+Li)$^+$, 313 (6), 160 (45), 91 (100).

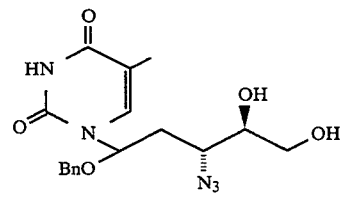

5-Benzyloxy-5-thymine-3 (S)-azido-1,2(S)-pentanediol (23).

To a 25 mL round-bottomed flask (flame dried and purged with argon) was added 3 (S)-Azido-5-dibenzyloxy-1, 2 (S)-pentanedibenzoate (22, 500 mg, 0.8840 mmole) and dichloroethane (6 mL). To this solution was added 2,4-bis(trimethylsilYl) thymine (239 mg, 0.8840 mmole) and trimethylsilyl trifluoromethane sulfonate (196 mg, 0.8840 mmole) under a dry argon atmosphere. The mixture was stirred at ambient temperature for @8 h (monitored by TLC) and quenched by dilution with wet ether (20 mL) and hexane (10 mL). The mixture was poured through a short plug of silica gel and the solvent removed in vacuo. The resulting white solid was further purified by flash chromatography (Rf=0.49, 50% EtOAc in hexane) to give 23 as a white crystalline solid of diastereomers (387 mg, 75% yield): $^1$H NMR (CDCl$_3$, diastereomeric mixture) d 1.83 (s, 3H, CH$_3$ on thymine), 1.87 (s, 3H, CH$_3$ on thymine), 2.07–2.17 (m, 4H), 3.75–3.81 (m, 1H), 4.08 (dt, 1H, J=3.3 Hz, Dn=11Hz), 4.47–4.74 (m, 8H), 5.49 (m, 1H), 5.57 (m, 1H), 6.01 (dd, 1H, J=3.7 Hz, Dn=9.6 Hz), 6.06 (t, 1H, J=6.3 Hz), 7.07 (s, 2H, vinylic H on thymine), 7.28–7.60 (m, 22H), 7.93–8.02 (m, 8H), 8.34 (s, 1H, NH on thymine), 8.38 (s, 1H, NH on thymine); $^{13}$C NMR (CDCl$_3$, diastereomeric mixture) d 12.40, 12.44, 36.01, 36.20, 58.92, 59.42, 62.22, 62.33, 71.60, 71.95, 73.05, 73.40, 81.48, 82.40, 111.77, 111.99, 128.14, 128.19, 128.35, 128.45, 128.50, 128.56, 128.90, 128.91, 129.18, 129.21, 129.52, 129.63, 129.75, 129.80, 133.21, 133.50, 133.90, 134.16, 135.60, 135.69, 150.74, 163.27, 163.37, 165.22, 165.28, 165.92.IR (Neat, diastereomeric mixture) 3190, 3070, 3040, 2960, 2950, 2110 (N$_3$), 1730–1675 (broad), 1440, 1350, 1305, 1270–1235 (broad), 1167, 1100–1090 (broad), 1057, 1015, 740, 700; LRFAB: 590 (M+Li)$^+$, 313 (45), 220 (12), 160 (100).

The crystalline solid was recrystallized from 1: 1.5 (ethyl acetate:hexane) to yield one diastereomer: mp 65°–66° C.; $^1$H NMR (CDCl$_3$) d 1.83 (s, 3H, CH$_3$ on thymine), 2.07–2.17 (m, 2H), 3.75–3.81 (m, 1H), 4.47–4.63 (AB q, 2H, J=11.7 Hz, Dn=33.2 Hz), 4.55 (dd, 1H, J=5.9 Hz, 10.3 Hz), 4.69–4.74 (dd, 1H, J=3.5 Hz, 12.2 Hz), 5.5 (m, 1H), 6.06 (t, 1H, J=6.3 Hz), 7.07 (s, 1H, vinylic H on thymine), 7.28–7.60 (m, 11H), 7.93–8.02 (dd, 4H, J=7.2 Hz, 20.0 Hz), 8.34 (s, 1H, NH on thymine).

Anal. Calcd for C$_{31}$H$_{29}$N$_5$O$_7$ (Diastereomeric mixture): C, 63.80; H, 5.01; N, 12.00. Found C, 63.66; H, 5.05; N, 11.79.

To a 25 mL round-bottomed flask was added the dibenzoate 23 (387 mg, 0.6630 mmole), powdered NaOH (55 mg, 1.375 mmole) and MeOH (6 mL). The mixture was stirred at ambient temperature for @3 h. The solvent was removed in vacuo and the resulting residue was dissolved in ethyl acetate (40 mL). The organic layer was washed 2 times with saturated sodium bicarbonate solution (2@20 mL), water (20 mL), and dried over anhydrous magnesium sulfate. The solvent was removed in vacuo to give 23 as a white solid (236 mg, 95% yield): mp 148° C.–150° C.; $^1$H NMR (CDCl$_3$) d 1.84 (s 3H, CH$_3$ on thymine), 1.99–2.08 (m, 1H), 2.14–2.22 (m, 1H), 3.17 (broad s, 1H, OH), 3.47–3.51 (m, 1H), 3.58 (m, 1H), 3.74 (m, 3H), (AB q, 2H, J=11.6 Hz, Dn=27.0 Hz), 6.02 (t, 1H, J=6.3 Hz), 7.15 (s, 1H, vinylic H on thymine), 7.30 (m, 5H), 9.68 (s, 1H, NH on thymine); IR (Neat, diastereomeric mixture) 3620–3125 (Broad), 3070, 3040, 2940, 2880, 2110, 1720–1660 (broad), 1470, 1455, 1430, 1400, 1365, 1260, 1215, 1075, 900, 750, 740, 700; LRFAB 382 (M+Li)+, 313 (20), 160 (100), 136 (27).

3'-Azido-3'-deoxythymidine. To a 10 mL round-bottomed flask was added azido diol 23 (100 mg, 0.2664 mmole) and CH$_3$OH (1 mL). The solution was cooled to −10° C. and a cooled (0° C.) solution of H$_2$SO$_4$ (1 mL, 9.38N in CH$_3$OH) was added dropwise. The mixture was allowed to warm to ambient temperature (over @2 h) and stirred at this temperature for 36 h. The mixture was diluted with CH$_3$OH, cooled to 0° C. and neutralized with sodium bicarbonate. The mixture was then filtered and solvent removed in vacuo. The resulting orange residue was dissolved in minimal amount of ethyl acetate and placed on a preparative TLC plate. Elution with 10:1 ethyl acetate afforded AZT (Rf=0.26) as a white powder (28.5 mg, 40% yield) and 23 (R$_f$=0.14) as a diastereomeric mixture (27 mg, 27% yield): mp 114°–115° C.; $^1$H NMR spectra, IR spectra, and chromatographic (TLC, HPLC) properties are identical to an authentic sample of AZT.

Example 2 Preparation of 3'-Fluorothymidine (FLT)

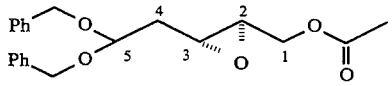

5,5-Dibenzyloxy-3(R),2(S)-oxo-1-O-acetylpentane
To a two-necked round-bottomed flask equipped with a magnetic spinbar and two rubber septa was added 0.59 g (0.00633 moles) 5,5-dibenzyloxy-3(R),2(S)-oxo-1-hydroxypentane, 0,005 g (0.0409 mmoles) N-dimethylaminopyridine, and acetic anhydride (15 mL). The mixture was allowed to stir at 25° C. for 12 hours. Excess acetic anhydride was removed in vacuo and the resulting residue was dissolved in diethyl ether (@150 mL). After washing with saturated sodium bicarbonate (2@25 mL) and brine @25 mL), the organic layer was dried over anhydrous magnesium sulfate. The organic layer was filtered and solvent removed in vacuo. The resulting oil was purified by silica gel flash chromatography (4:1 hexanes:ethyl acetate) to give 5,5-dibenzyloxy-3(R),2(S)-oxo-1-O-acetylpentane (96%, 0.645g) as a colorless oil. This procedure can be scaled-uP with minimum decrease in yield.

5,5-Dibenzyloxy-3 (R), 2 (S)oxo-1-O-acetylpentane: Spectral and physical Data:

Physical data: Colorless Oil; R$_f$ 0.31 (4:1 hexanes:ethYl acetate).

$^1$HNMR: (300.1 MHz, CDCl$_3$) δ7.33 ( broad s, 10H, phenyl), 4.93 (t,1H, J=5.6, H-5), 4.73–4.54 (m, 4H, benzylic), 4.35, 4.31 (dd, 1H, J=2.6, 12.3, H-1), 3.90, 3.88 (dd, 1H, J=6.0, H-1), 3.00 (m, 2H, H-2,3), 2.06 (s, 3H, acetate), 2.11–1.90 (m, 2H, H,H'-4).

$^{13}$CNMR: (75.5 MHz, CDCl$_3$) δ170.01 (acetate C=O); 137.29,127.92, 127.20 (phenyl); 99.28 (C-5); 67.64, 66.98 (benzylic); 63.84 (C-1); 54.54, 52.22 (C-2,3); 35.62 (C-4); 20.14 (acetate CH$_3$).

IR: (neat): 3090(m), 3070(m), 3035(m), 2930(m), 2875(m), 1740(s, acetate C=O), 1505(m), 1457(m), 1390(m), 1370(m), 1230(s), 1125(s), 1040(s), 1025(s), 890(m), 740(s), 700 cm$^{-1}$(s).

MS: (low resolution FAB) m/e 363 (M+Li)+313(32), 249(10), 220 (25), 136 (50).

EA: Calculated for C$_{21}$H$_{24}$O$_5$: C,70.77; H,6.79;. Found: C,70.52 ; H,6.83.

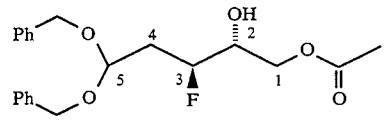

5,5-Dibenzyloxy-3(S)-fluoro-2(R)-hydroxyl-1-O-acetylpentane: Procedure 1.

To a two-necked round-bottomed flask equipped with reflux condenser with argon inlet, magnetic spinbar, and rubber saprum was added 3.5 g (0.007 moles) 5,5-dibenzyloxy-3(R), 2(S)-oxo-1-O-acetylpentane, 4.4 g (0.015 moles) tetrabutylammonium dihydrogentrifluoride and 7.7 g (0.098 moles) potassium hydrogendifluoride. Under an argon atmosphere the flask containing the mixture was immersed into silicon oil bath at 100° C. With vigorous stirring the bath temperature was increased to @120° C. The mixture was allowed to stir for approximately 20 hours (monitored by thin layer chromatography, 2:1 hexane:ethyl acetate) at 120° C. which effected a gradual color change from a dull yellow to black. After cooling to 25° C., the black residue was dissolved in 1:1 hexanes:ethyl acetate @250mL) and washed with saturated sodium bicarbonate solution (3@75mL), and brine (75 mL). To the organic layer was added magnesium sulfate and Norit decolorizing charcoal. After stirring for @10 min., the organic layer was poured through a short plug (@3×3cm) of silica gel. The solvent was removed in vacuo and the resulting residue was purified by silica gel flash-chromatography (2:1 hexanes:ethyl acetate) to yield 5,5-dibenzyloxy-3-fluoro-2-hydroxy-1-O-acetylpentane (58%, 2.15g, 25:1 C-3:C-2 epoxide opening) as a colorless oil and 5,5-dibenzyloxy-3(S)-fluoro-2(R)-1-1-hydroxylpentane (15%, 0.50 g).

5,5-Dibenzyloxy-3(S)-fluoro-2(R)-hydroxyl-1-O-acetylpentane: Procedure 2.

To a two-necked round-bottomed flask equipped with reflux condenser with argon inlet, magnetic spinbar and rubber septum was added 3.10 g (0.0103 moles) tetrabutylammonium dihydrogen-trifluoride and 2.80 g (0.0079 moles) 5,5-dibenzyloxy-3(R),2(S)-oxo-1-O-acetylpentane. Under an argon atmosphere the flask containing the reaction mixture was immersed into a silicon oil bath (150°–160° C.). The reaction mixture was allowed to stir for approximately 2 hours (monitored by thin layer chromatography, 2:1 hexane:ethyl acetate) at 150° C. After cooling to 25° C. the black residue was dissolved in 1:1 ethyl acetate:hexane (80 mL) and washed with saturated sodium bicarbonate solution (2@30 mL) and brine (30mL). To the organic layer was added magnesium sulfate and Norit decolorizing charcoal. After stirring for @10 min., the organic layer was poured through a short plug (@3×3cm) of silica gel. The solvent was removed in vacuo and the resulting residue was purified by silica gel flash-chromatography (2:1 hexanes:ethyl acetate) to yield 5,5-dibenzyloxy-3(S)-fluoro-2(R)-1-O-acetylpentane (62%, 1.87g, 25:1C-3:C-2 epoxide opening) as a colorless oil. A 25:1 ratio of C-3:C-2 epoxide opening was determined by GC analysis on the aminal diacetate derivative.

5,5-Dibenzyloxy-3(S)-fluoro-2(R)-hydroxyl-1-O-acetylpentane: Spectral and physical Data:

Physical data: Colorless Oil; $R_f$ 0.24 (2:1 hexanes:ethyl acetate).

$^1$HNMR: (300.1 MHz, $d_6$-benzene) $\delta$7.27 (d, 4H, phenyl), 7.17-7.10 (m under solvent signal, 6H, phenyl), 5.03 1, 1H, (q, J=3.8, H-5), 4.75, 4.58 (dtd, 1H, $\Delta\nu$=47.9, J=2.7, 2.4, H-3, downfield dtd under benzylic signal), 4.58-4.34 (m, 4H, benzylic), 4.13 (d, unresolved ddd, 1H, J=11.8, H-1), 4.00 (ddd, 1H, J=0.90, 5.89, 11.76, H-1), 3.60 (m, 1H, H-2), 2.31, 2.20 (dddd, 1H, J-2.7, 7.8, 14.8, 35.30, H-4), 2.14-2.00 (m, 1H, H'-4, under hydroxyl signal ), 2.12 ( d, 1H, 5.6, OH), 1.55 (s, 3H, acetate).

$^{13}$C NMR: (75.5 MHz, CDCl$_3$): $\delta$171.23 (Acetate C-O); 137.62, 137.52, 128.42, 128.40, 127.74, 127.72 (Phenyl); 98.97, 98.92 (d, J-3.7, C-5); 91.11, 88.84 (d, J=171.8, C-3); 70.86, 70.54 (d, J=24.20, C-2); 68.03, 67.84 (Benzylic); 64.77, 64.70 (d, J=5.1, C-1), 35.43, 35.17 (d, J=20, C-4), 20.71 (Acetate CH$_3$).

IR: (neat) 3710-3230 (Broad, OH), 3090(w), 3070(m), 3030(m), 2940(m), 2870(m), 1740(s), 1505(m), 1460(m), 1375 (broad), 1240(s), 1125(s), 1045(s), 1025(s), 740(s), 700 cm$^{-1}$(s).

MS: (low resolution FAB) m/e 393 (M+Li)+363(5), 321(5), 275(10), 255(5), 181(15), 161(48), 127(14).

EA: Calculated for C$_{21}$H$_{25}$FO$_5$: C,67.01; H,6.69. Found: C,66.85; H,6.74.

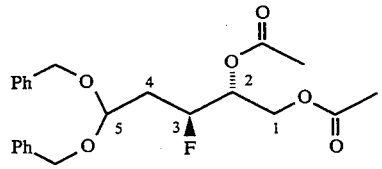

5,5-Dibenzyloxy-3(S)-fluoro-Z(R)-1-O-diacetylpentane

To a two-necked round-bottomed flask equipped with a magnetic spinbar and two rubber septa was added 0.50g (0.00133 moles) 5,5-dibenzyloxy-3(S)-fluoro-2(R)-hydroxyl-1-O-acetylpentane, (0.005g (0.0409) moles) N-dimethylaminopyridine, and acetic anhydride (15mL). The mixture was allowed to stir at 25° C. for 20 hours. Excess acetic anhydride was removed in vacuo and the resulting residue was dissolved in diethyl ether (@150mL). After washing with saturated sodium bicarbonate (2@25mL) and brine @25mL), the organic layer was dried with anhydrous magnesium sulfate. The organic layer was filtered and solvent removed in vacuo. The resulting oil was purified by silica gel flash-chromatography (4:1 hexanes:ethyl acetate) to give 5,5-dibenzyloxy-3(R)-fluoro-2(R)-1-O-diacetylpentane (95.2%, 0.530g) as a colorless oil.

5,5-Dibenzyloxy-3(S)-fluoro-2(R)-1-diacetopentane: Spectral and Physical Data:

Physical Data: colorless oil; $R_f$0.32 (4:1 hexanes:ethyl acetate).

$^1$H MMR: (300.1 MHz, de-benzene) $\delta$7.27 (d, 3H, J=7.4, phenyl); 7.19-7.07 (m, 7H, phenyl); 5.31 (m, 1H, H-2); 5.02, 4,85, (q, 1H, $\Delta\nu$=50.8, J=6.0, H-3); 4.96 (dd, 1H, J=5.7, 0.5, H-5); 4.54 (d, 1H, J-11.8, benzylic); 4.48 (d, 1H, J-11.8, benzylic; 4.37 (d, 2H, J=11.8, benzylic); 4.41 (s, 1H, H-1); 4.05 (dd, 1H, J=6.6, 11.6, H-1) 2.13 (t, 1H, J=6.0, H-4); 2.04 (m, 1H, H-4); 1.58 (s, 3H, acetate C=O); 1.57 (s, 3H, acetate C=O).

$^{13}$C MMR: (75.5 MHz, CDCl$_3$): $\delta$170.19, 169.56 (acetate C=O); 137.54, 137.49, 128.23, 127.56, 127.52 (phenyl); 98.82, 98.78 (d, J=3.4, C-5); 89.66, 87.36 (d, J=17.3, C-3); 71.62, 71.30 (d, J=24, C-2); 68.19, 67.72 (benzylic); 61.29; 61.20 (d, J=6.6, C-1); 35.55, 35.29 (d, J=20.1, C-4); 20.55, 20.39 (acetate CH$_3$).

IR: (neat) 3065(m), 3030(m), 2935(m), 2870(m), 1745(s), 1496(m), 1450(m), 1430 (shoulder), 1365(s), 1240-1210 (s, broad), 1120 (shoulder), 1060-1020 (s, broad), 740(s), 700 cm$^{-1}$(s).

MS: (low resolution FAB) m/e 425 (M+Li)+405 (+Li-HF)+,363 (10).

EA: Calculated for C$_{23}$H$_{27}$FO$_6$: C, 66.02; H, 6.50; F, 4.54. Found: C, 65.85; H, 6.64; F, 4.28.

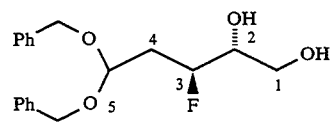

5,5-Dibenzyloxy-3(S)-fluoro-2(R)-1-dihydroxylpentane

To a two-necked round-bottomed flask equipped with reflux condenser with argon inlet, magnetic spinbar and rubber septum was added 0.72 g (0.0024 moles) tetrabutylammonium dihydrogen-trifluoride, 1.24 g (0.0159 moles) potassium hydrogendifluoride and 0.5 g (0.00159 moles) 5,5-dibenzyloxy-(R),2(S)-oxo-1-hydroxylpentane. Under an argon atmosphere the flask containing the reaction mixture was immersed into a silicon oil bath. With stirring the bath temperature was increased to −120°-123° C. The reaction mixture was allowed to stir for @24 hours (monitored by tlc, 5:5 hexane:ethyl acetate) at 120°-123° C. After cooling to 25° C., the brown residue was dissolved in ethyl acetate (50 mL) and washed with water (40 mL), saturated sodium bicarbonate solution (2×40 mL), and brine (40 mL). To the organic layer was added magnesium sulfate and Norit decolorizing charcoal. After stirring for approximately 20 minutes, the organic layer was poured through a short plug (@3×3 cm) of silica gel. The solvent was removed in vacuo and the resulting residue was purified by silica gel flash-chromatography (1:1 hexanes:ethyl acetate) to yield 5,5-dibenzyloxy-3(S)-fluoro-(R)-1-hydroxylpentane (71.5%, 0.38g) as a white gum.. A 4.5:1 ratio of C-3:C-2 epoxide opening was determined by GC analysis on the diacetate derivative.

5,5-Dibenzyloxy-3(S)-fluoro-2(R)-1-dihydroxylpentane: Spectral and Physical Data:

Physical data: White gum; $R_f$0.25 (1:1 hexanes:ethyl acetate).

$^1$HNMR: (300.1 MHz, CDCl$_3$) 6 7.34 (s, 10H, phenyl); 5.01 (dd, 1H, J=6.3, 1.5, H-5); 4.76, 4.63 (dt, 1H, $\Delta\nu$=49.1, J=6.9, 3.8, H-3); 4.68 (dd, 2H, J=11.6, 2.7, benzylic); 4.61 (dd, 2H, J-11.6, 2.9, benzylic); 3.73 (m, 3H, H-2, H-1); 2.72 (s, 1H, OH); 2.15 (m, 2H, H-4 ); 1.85 ( s, 1H, OH).

$^{13}$C NMR: (75.5 MHz, CDCl$_3$): δ137.62, 128.49, 128.42, 127.82, 127.79, 127.74 (phenyl); 99.28, 88.24 (J=3.11, C-5); 91.41, 89.15 (J=170.4, C-3); 72.80, 72.49 (J=23.6, C-2); 68.17, 67.79 (benzylic); 62.46, 62.40 (J=5.2, C-1); 35.57, 35.30 (J=20.1, C-4) .

IR: (neat) 3700–3100 (Broad, OH), 3080(w), 3040(w), 3020(w), 2915(m), 2850(m), 1735(m), 1495(s), 1445(s), 1375(m), 1350(m), 1245(m), 1210(m), 1120–1010 (broad), 730(s), 690 cm$^{-1}$(s).

MS: (low resolution FAB) m/e 341.2 (M+Li)$^+$, 233.1(10), 213.1(5).

EA: Calculated for C$_{19}$H$_{23}$FO$_4$: C, 68.25; Found: C, 67.71; H, 6.98.

HRMS: ( FAB ) Calculated for C$_{19}$H$_{23}$FO$_4$Li: 341.1740. Found: 341.1735.

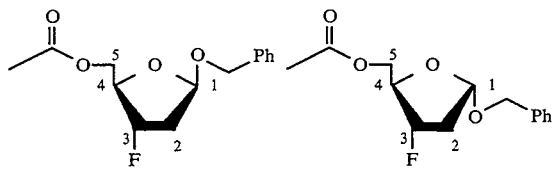

1-Benzyloxy-3-fluoro-4-methyleneacetate furan

To a round-bottomed flask equipped with magnetic spinbar and rubber septum was added 0.20 9 (0.5315 mmoles) 5,5-dibenzyloxy-S(S)-fluoro-2(R)-1-O-acetylpentane and CH$_2$Cl$_2$ (3.5 mL). Under an argon atmosphere the flask with this solution was immersed into an ice/water bath and 0.09 mL (0.7970 mmoles) SnCl$_4$ was added dropwise. The mixture was allowed to warm to room temperature. After stirring at room temperature for @1.5 hours, the reaction mixture was quenched with water (3 mL) and NEt$_3$ (3 mL). The mixture was diluted with ether (100 mL) and washed with water (2@30mL). After drying the organic layer with magnesium sulfate and filtering solution, the solvent was removed in vacuo to yield 1-benzyloxy-3-fluoro-4-methyleneacetate furan as a 1.4:1 mixture of α,β anomers. The anomers were separated and purified by silica gel flash-chromatography (3:1 hexanes:ethyl acetate) to give a 1-α-benzyloxy-3-fluoro-4-methyleneacetate furan (49.1%, 70 mg) and 1-β-benzyloxy-3-fluoro-4-methyleneacetate furan (35.1%, 50 mg) as colorless oils.

1-Benzyloxy-3-fluoro-4-methyleneacetate furan: Procedure 2:

To a round-bottomed flask-equipped with magnetic spinbar and rubber septum was added 0,275 g (0.7306 mmoles) 5,5-dibenzyloxy-3(S)-fluoro-2(R)-1-O -acetylpentane and CH$_2$Cl$_2$ (7.0 mL). Under an argon atmosphere the flask with this solution was immersed into a dry ice/ethylene glycol bath (@−23° C.) and 0.11 mL (0.9133 mmoles) SnCl$_4$ was added dropwise. After 5 minutes at −23° C. thin layer chromatography indicated complete reaction. The reaction mixture was quenched at −23° C. with NEt$_3$ (4 mL) and water (3 mL). The mixture was diluted with ether (100 mL) and washed with water (2@40 mL). After drying the organic layer with magnesium sulfate and filtering, the solvent was removed in vacuo to yield 1-benzyloxy-3-fluoro-4-methyleneacetate furan as a 1:4.6 mixture of α,β anomers. The anomers were separated and purified by silica gel flash-chromatography (3:1 hexanes:ethyl acetate) to give 1-α-benzyloxy-3-fluoro-4-methyleneacetate furan (13.3%, 26mg) and 1-β-benzyloxy-3-fluoro-4-methyleneacetate furan (61%, 120mg) as colorless oils.

1-α-Benzyloxy-3-fluoro-4-methyleneacetate furan: Spectral and Physical Data:

Physical data: Colorless oil; R$_f$0.32 (3:1 hexanes:ethyl acetate).

$^1$H NMR: (361MHz, CDCl$_3$) δ7.34–7.27 (m, 5H, phenyl); 5.40 (AB q, J=5.2, 3.3, 1H, H-1); 5.28, 5.10 (2 symmetrical m, Δν=57, 1H, H-3); 4.75 (d, J-11.5, 1H, benzylic); 4.47 (d, J-11.5, 1H, benzylic); 4.44, 4.37 (dtd, J=20.1, 6.2, 0.9, 1H, H-4), 4.22 (dd, J=11.5, 6.6, 1H, H-5); 4.13 (dd, J=11.7, 5.9, 1H, H'-5); 2.47–2.32 (m, 2H, H-2', H-2''); 2.04 (s, 3H, acetate CH$_3$)

$^{13}$C NMR: (75.5 MHz, CDCl$_3$): δ170.46 (C=O); 137.30; 128.36, 127.91, 127.74 (phenyl). 103.75 (C-1); 95.41, 93.02 (d, J=180, C-3); 82.21, 81.87 (d, J=25.7, C-4), 69.84 (benzylic), 63.84, 63.71 (d, J=10, C-5); 39.82, 39.54 (d, J-21, C-2); 20.74 (acetate CH$_3$).

IR: (Neat) 3065(w), 3035(m), 2945(s), 1740(vs), 1502(m), 1457(s), 1435(s), 1367(s), 1230(vs), 1105(vs), 1035(vs), 960(s), 915(s), 740(s), 700 cm$^{-1}$(s).

MS: (low resolution FAB) m/e 275 IM+-Li)+255(10), 181(10), 161(55), 137(20), 107(15), 91(100).

MRMS: ( FAB ) Calculated for C$_{14}$H$_{17}$FO$_4$Li: 275.1271. Found: 275.1280.

1-β-Benzyloxy-3-fluoro-4-methyleneacetate furan: Spectral and Physical Data:

Physical data: Colorless oil; R$_f$ 0.50 (3:1 hexanes: ethyl acetate).

$^1$H NMR: (361MHz, CDCl$_3$) δ7.35–7.28 (m, 5H, phenyl); 5.31 (d, J=5 .0, 1H, H-1); 5.13, 4.98 (dd, Δν=55.5, 5.9, 1H, H4.83 (d, J=12.2, 1H, benzylic); 4.57 (d, J=12.3, 1H, benzylic ); 4 .54, 4.46 (d of multiplets, J=25.3, 1H, H-4), 4.20 (m, 2H, H,H-5'); 2.39–2.12 (m, 2H, H,H'-2); 2.08 (s, 3H, acetate CH$_3$).

$^{13}$C NMR: (75.5 MHz, CDCl$_3$) δ170.46 (C=O); 137.30, 128.29, 127.68, 127.51 (phenyl), 102.78 (C-I); 94.54, 92.14 (d, J=181.1, C-3); 81.57, 81.21 (d, J=27.1, C-4), 69.00 (benzylic), 63.47, 63.35 (d, J-8.9, C-5); 39.69, 39.41 (d, J=20.8, C-2); 67 (acetate CH$_3$) .

IR: (Neat) 3065 (w) , 3035 (m) , 2945 (s) , 1740 (rs) , 1502(m), 1457(s), 1428(s), 1367(s), 1235(vs), 1083(vs), 1037(vs), 1003(s) , 940(s), 740(s), 700 cm$^{-1}$(s).

MS: (low resolution FAB) m/e 275 (M+Li)$^+$, 255(10) 181(10), 161 (55), 137 (20), 107 (15), 91 (100) .

HRMS: (FAB) Calculated for C$_{14}$H$_{17}$FO$_4$Li: 275.1271. Found: 275. 1269.

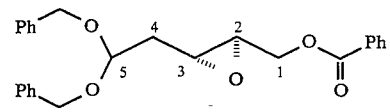

5,5-Dibenzyloxy-3(R), 2(S)-oxo-1-O-benzaylpentane: Procedure

To a three-necked round-bottomed flask equipped with magnetic, spinbar, rubber septum, and argon inlet was added 1.0 g (0.00318 moles) 5,5-dibenzyloxy-3(R), 2(S)-oxo-1-hydroxylpentane and CH$_2$Cl$_2$ (20 mL). To this solution at room temperature under argon was added 1.33 mL (0.00954 moles) triethylamine, 0.015 mg (0.1228 moles) 4-dimethylaminopyridine, and 0.46 mL (0.00398 moles) benzoyl chloride. The mixture was allowed to stir at room temperature for @2 hours with monitoring by thin layer chromatography. The CH$_2$Cl$_2$ was removed in vacuo and the resulting residue was dissolved in 4:1 hexanes:ethYl acetate (150mL) and washed with water (2@50mL) and saturated sodium bicarbonate solution (2@50mL). The organic layer was dried over magnesium sulfate and solvent removed in vacuo. The resulting orange oil was purified by silica gel flashchromatography (4:1 hexanes:ethyl acetate) to give 5,5-dibenzyloxy-3(R), 2(S)-oxo-1-O-benzoylpentane (94%, 1.25g) as a colorless oil.

5,5-DibenzyloxY-3(R), 2(S),oxo-1-O-benzoylPentanePhysical and Spectral Data:

Physical data: Colorless oil; $R_f$=0.32 (4:1 hexanes: ethyl acetate).

$^1$H NMR: (300.1 MHz, CDCl$_3$) δ8.05 (d, 2H, J=7.2, phenyl); 7.56–7.32 (m, 13H, phenyl); 4.95 (dd, 1H, J=6.2, 1.1, H-4.69 (m, 4H, benzylic); 4.56 (ddd, 1H, J=2.0, 5.1, H-1); 4.15 (dd, 1H, J=5.9, 12.3, H-1); 3.13 (m, 2H, H-3, H-2); 2.08 (dddd, 1H, J=14.4, 6.4, 1.7, H-4); 2.00 (dddd, 1H, J=15.8, 6.5, 1.4, H-4).

$^{13}$C NMR: (75.5 MHz, CDCl$_3$) 165.52 (benzoate carbonyl); 137.50, 132.65, 129.26, 129.22, 127.98, 127.94, 127.25 (phenyl); 99.44 (C-5); 67.66, 67.07 (benzylic); 64.28 (C-1); 54.73, 52.24 (C-3, C-2); 35.75 (C-4).

IR: (Neat) 3070 (m); 3030 (m); 2930 (m); 2870 (m); 1720(s); 1615 (m); 1600 (w); 1455 (m); 1395 (m); 1350 (m); 1340 (m); 1320 (m); 1270 (s); 1220 (w); 1185 (m); 1110 (s); 1070 (s); 1045 (s); 1020 (s); 900 (m); 740 (s); 710 (s); 700 cm$^{-1}$ (s).

MS: (low resolution FAB) m/e 425 (M+Li)$^+$, 363(15), 303 (10), 227 (5), 195 (5).

EA: Calculated for C$_{26}$H$_{26}$O$_5$: C, 74.62; H, 6.26. Found: C, 74.51; H, 6.31.

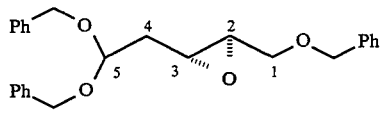

5,5,1-Tribenzyloxy-3(R),2(S)-oxopentane.

To a three-necked round-bottomed flask equipped with a magnetic spinbar, two rubber septa, an argon outlet was added 0.55 g (0.0137 moles, 60% dispersion in mineral oil) NaH and THF (50 mL). The mixture was cooled to 0° C. with an ice bath under an argon atmosphere and THF (10mL) of 3.3g (0.0105 moles) 5,5-dibenzyloxy-3(R), 2(S)-oxo-1-hydroxylpentane added dropwise over a 10 minute period. After stirring for 10 minutes at 0° C., 0.7? (0.00210 moles) tetrabutylammonium iodide and 1.5 mL (0.0126 moles) benzyl bromide were added with gradual warming to room temperature. The mixture was allowed to stir for @3.5 hours with monitoring by thin layer chromatography. The mixture was quenched with saturated ammonium chloride (20 mL) and THF was removed in vacuo. The resulting residue was dissolved in ether @150 mL) and washed with water (2@100 mL). The organic layer was dried over anhydrous magnesium sulfate and the ether was removed in vacuo. The resulting oil was purified by silica gel flash-chromatography (3:1 hexanes:ethyl acetate) to give 5,5,1-tribenzyloxy-3(R), 2(S)-oxopentane (82%, 3.45g) as a colorless oil.

5,5,1-Tribenzyloxy-3(R), 2(S) -oxopentane. Physical and Spectral Data:

Physical data: Colorless oil; $R_f$=0.43 ( 3: 1 hexanes: ethyl acetate).

$^1$H NMR: (300.1 MHz, CDCl$_3$) δ7.31 (broad s, 15H, phenyl); 4.92 (dd, 1H, J=5.96, 0.6, H-5); 4.71–4.53 (m, 6H, benzylic); 3.65 (dd, 1H, J=2.8, 11..5, H-1); 3.41 (dd, 1H, J=5.3, 11.5, H-1); 2.97 (t, 2H, J=4.7, H-3, H-2); 2.03 (m, 1H, H-4); 1.95 (m, 1H, H-4).

$^{13}$C NMR: (75.5 MHz, CDCl$_3$) δ137.56, 128.03, 127.98, 127.32, 127.27 (phenyl); 99.63 (C-5); 72.67 (benzylic at C-1); 69.73 (C-1); 67.69, 67.06 (benzylic); 56.37 (C-2), 51.84 (C-3); 35.91 (C-4).

IR: (Neat) 3090(w), 3070(w), 3030(m), 2930(m), 2870(s), 1615(w), 1600(w), 1500(m), 1460(s), 1360(m), 1215(m), 1120(s), 1045(s), 1025(s), 740(s), 700cm$^{-1}$ (s).

MS: (low resolution FAB) m/e 411 (M+Li)$^+$.

EA: Calculated for C$_{26}$H$_{28}$O$_4$: C, 77.20; H, 6.98. Found: C, 77.03; H, 6.88.

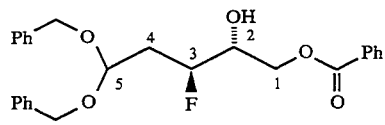

5,5-Dibenzyloxy-3(S)-fluoro-2(R)-hydroxyl-1-O-benzoylpentane. Procedure 1.

To a round-bottomed flask equipped with a magnetic spinbar and an argon inlet was added 2.0 g (0.00478 moles) 5,5-dibenzyloxy-3(R),2(S)-oxo-1-O -benzoylpentane, 1.44 g (0.00478 moles) tetrabutyammonium dihydrogen-trifluoride, and 1.87 g (0.0239 moles) potassium hydrogendifluoride. Under an argon atmosphere the mixture was immersed in an oil bath (@150° C.) and allowed to stir for @2.5 hours (monitored by tlc). Cooled to room temperature, the resulting black gum is dissolved in 1:1 hexanes:ethyl acetate (@250mL) and washed with saturated sodium bicarbonate solution (2@50mL) and brine (@100mL). The organic layer was dried over anhydrous magnesium sulfate and the solvent removed in vacuo. The resulting dark brown oil was purified by silica gel chromatography (2:1 hexanes:ethyl acetate) to give 5,5-dibenzyloxy-3(S)-fluoro-2(R)-hydroxyl-1-O-benzoylpentane (71%, 1.5 g) as a colorless oil. The silica gel column was then eluted with 1:1 hexanes:ethyl acetate to give 5,5-dibenzyloxy-3(S)-fluoro-2(R)-1-dihydroxylpentane (@5.6%, 90 mg).

Procedure 2:

To a round-bottomed flask equipped with a magnetic spinbar and an argon inlet was added 2.05 g (0.00490 moles) 5,5-dibenzyloxy-3,2-oxo-1-O-benzoylpentane and 2.21 g (0.00735 moles) tetrabutylammonium dihydrogen-trifluoride. Under an argon atmosphere the mixture was immersed in an oil bath (160°–170° C.) and allowed to stir for @1 hour (monitored by tlc). Cooled to room temperature, the resulting black gum is dissolved in 1:1 hexanes:ethyl acetate (@250mL) and washed with saturated sodium bicarbonate solution (2@150mL) and brine (@100mL). The organic layer was dried over anhydrous magnesium sulfate and filtered. After removal of the solvent in vacuo, the resulting dark brown oil was purified by silica gel chromatography (2:1 hexanes:ethyl acetate) to give 5,5-di-benzyloxy-3(S)-fluoro-2(R)-hydroxyl-1-O-benzoylpentane (83%, 1.8g) as a colorless oil. A 15:1 ratio of C-3:C-2 epoxide opening was determined by GC analysis on the aminal diacetate derivative.

5,5-Dibenzyloxy-3(S)-fluoro-2(R)-hydroxyl-1-benzoylpentane. Physical and Spectral Data.

Physical data: Colorless oil; $R_f$ =0.45 (2:1 hexanes: ethyl acetate).

$^1$H NMR: (300.1 MHz, CDCl$_3$) δ8.03 (d, 2H, J=7.6, phenyl); 7.61-7.28 (m,13H, phenyl); 5.05 (dd, 1H, J=7.0, 2.6, H-5); 4.86 (dtd, ½ H, J=3.1, 2.8) and 4.70 (dtd under benzylic proton signal, ½H, Δν=49.9, J=3.1.2.8, H-3); 4.70 (dd, 2H, J=5.9, 11.6, benzylic); 4.62 (d, 2H, J=11.6, benzylic); 4.55 (dd, 1H, J=2.2, 11.8, H-1); 4.40 (dd, 1H, J=5.9, 11.8, H-1); 4.03 (m, 1H, H-2); 2.80 (d, 1H, J=5.3, OH); 2.35 (ddd, 1H, J=3.0, 7.2, 14.8, H-4); 2.25 (m, 1H, H-4).

13C NMR: (75.5 MHz, CDCl3) δ166.89 (benzoate carbonyl); 137.83, 137.81, 133.34, 129.81, 129.72, 128.34, (phenyl); 99.26, 99.22 (J=3.2, C-5); 91.49, 89.22 (J=171.5, C-3); 71.12, 70.81 (J=23.9, C-4); 68.21, 67.93 (benzylic); 65.38, 65.32 (J=5.0, C-1); 35.57, 35.31 (J=20.1, C-4).

IR: (Neat) 3470(broad), 3070 (m), 3040 (m), 2940 (m), 2880(m), 1725 (s), 1620 (m), 1600 (w), 1510 (m), 1460 (s), 1395 (m), 1365(m), 1325 (m), 1275 (s), 1190 (m), 1120 (s), 1050 (s), 1030 (s), 745(s), 715 cm⁻¹ (s).

MS: (low resolution FAB) m/e 445 (M+Li)+, 205 (10).

EA: Calculated for $C_{26}H_{26}O_5$: C, 71.22; H, 6.21. Found: C, 77.00; H, 6.22.

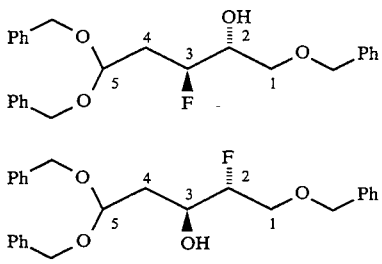

5,5,1-Tribenzyloxy-3(S)-fluoro-2(R)-hydroxylpentane and
5,5,1-tribenzyloxy-3(S)-hydroxyl-2(R)-fluoropentane.

To a round-bottomed flask equipped with a magnetic spinbar and an argon inlet was added 2.0 g (0.00494 moles) 5,5,1-tribenzyloxy-3(R)-1(S)-oxopentane and 2.24 g (0.00742 moles) tetrabutylammonium dihydrogen-trifluoride. Under an argon atmosphere the flask with mixture was immersed in an oil bath (@140° C.) and allowed to stir for @1 hour (monitored by tlc). The temperature of the oil bath was increased (@150° C.) and the black mixture was stirred for an additional 2 hours. Cooled to room temperature, the resulting black gum was dissolved in 1:1 hexanes:ethyl acetate (@250mL) and washed with saturated sodium bicarbonate solution (2@150mL) and brine (@100mL). The organic layer was dried over anhydrous magnesium sulfate and filtered. After removal of solvent in vacuo, the resulting black oil was purified by silica gel flash-chromatography (3:1 hexanes:ethyl acetate) to give an inseparable @1:1 mixture of 5,5,1-tribenzyloxy-3(S)-fluoro-2(R)-hydroxylpentane and 5,5,1-tribenzyloxy-3(R)-hydroxyl-2(S)-fluoropentane (60%, 1.25g) as a colorless oil and 5,5,1-tribenzyloxy-3 (R)-2(S)-oxopentane (10%, 210 mg). A 1.4:1 ratio of C-3:C-2 epoxide opening was determined by GC analysis of the acetate derivative.

5,5,1-Tribenzyloxy-3(S)-fluoro-2(R)-hydroxylpentane and
5,5,1-tribenzyloxy-3(R)-hydroxyl-2(S)-fluoropentane. Physical and Spectral Data:

Physical data: Colorless oil; two regioisomers are chromatographically inseparable, $R_f$ 0.27 (3:1 hexanes:ethyl acetate).

1H NMR: (300.1 MHz, CDCl3) δ7.35 (broad s, 15H, phenyl); 5.02 (m, 1H, H-5); 4.79 (dtd, 0.5H, J=2.6, 3.0) and 4.70 (dtd under benzyl proton signal, 0.5H, Δν=49.9, H-3); 4.70 (dt, 2H, J-5.1, 10.4, benzylic); 4.58 (m, 4.5H, benzylic and H-2 of 2-fluoro isomer); 4.40 (m, 0.5H, H-2 of 2 - fluoro isomer); 4.07 (m, 1H, H-3 in 2-fluoro isomer); 3.86 (m, 1H, H-2 in 3-fluoro isomer); 3.75 (dd, 2H, J=3.1, 25.9, H- 1 in 2 - fluoro isomer); 3.60 (m, 2H, H-1 in 3-fluoro isomer); 3.15 (d, 1H, J=3.3, OH); 2.50 (d, 1H, J=5.4, OH); 2.35 (dddd, 1H, J=2.6, 7.7, H-4 in 3-fluoro isomer); 2.13 (m, 2H, H-4, in 2-fluoro isomer); 1.92 (m, 1H, H-4 in 3 - fluoro isomer).

13C NMR: (75.5 MHz, CDCl3) δ137.71, 137.56, 137.49, 137.46, 137.34, 128.27, 128.21, 127.58 (phenyl); 100.62 (C-5 in 2-fluoro isomer); 99.07, 99.05 (J=1.7, C-5 in 3-fluoro isomer); 94.99, 92.67 (J-175.1, C-2 in 2-fluoro isomer); 91.32, 89.06 (J=170.6, C-3 in 3-fluoro isomer); 73.27, 73.18 (J=7.2, C-1 in 3fluoro isomer); 71.29, 70.97 (J=23.69, C-2 in 3-fluoro isomer); 69.94, 69.87 (J=5.0, C- 1 in 3 - fluoro isomer); 69.00, 68.72 (J=21.3, C-3 in 2 - fluoro isomer); 68.26, 67.68, 67.31 (benzylic); 67.26, 66.95 (C-3 in 2-fluoro isomer); 35.71, 35.67 (J=2.9, C-4 in 2-fluoro isomer); 35.18, 34.92 (J=19.9, C- 4 in 3 - fluoro isomer)/

IR: (Neat) 3460 (broad), 3090 (w), 3060 (m), 3030 (m), 2920 (m), 2860 (m), 2250 (w), 1725 (m), 1505 (m), 1455 (s), 1365 (m), 1320(w), 1275 (w), 1220 (m), 1110 (s), 1040 (s), 1020 (s), 910 (s), 730(s), 695 cm⁻¹ (s).

MS: (low resolution FAB) m/e 431.5 (M+Li) +, 233 (5), 189(8).

EA: Calculated for $C_{26}H_{26}O_5$: C, 73.56; H, 6.89. Found: C, 73,43; H, 6.92.

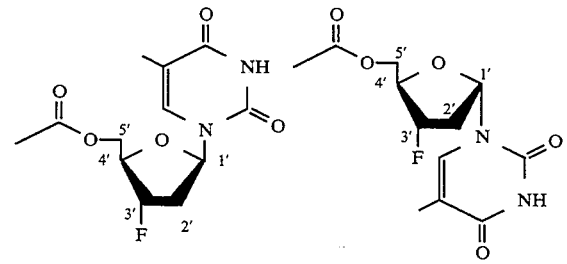

1-(5-O-Acetyl-3-fluoro-2,3-dideoxy-β-D-erythro-pentofuranosyl) thymine and 1-(5-O-acetyl-3-fluoro-2,3-dideoxy-α-D-erythro-pentofuranosyl) thymine.

To a round-bottomed flask equipped with a magnetic spinbar, rubber septum, and an argon inlet was added 120 mg (0.3190 moles) 5,5-dibenzyloxy-3 (S) -fluoro-2 (R) -hydroxyl-1-O-acetylpentane, 0.17 g (0.6400 moles) of 2,4 bis-O-trimethylsilylthymine and CH3CN (1.5 mL). At room temperature with vigorous stirring, 0.124 mL (0. 6400 mmoles) trimethylsilyl trifluoromethane sulfonate was added dropwise. The mixture turned from milky white to transparent yellow and then gradually to dark brown. The mixture was allowed to stir for 2.75 hours at room temperature. The reaction was quenched with wet ether (1 mL) and NEt3 (1 mL). With 2:1 ethyl acetate:hexanes the mixture was eluted through a short plug of silica gel. After removal of the solvent in vacuo the resulting residue was analyzed by 1H NMR to reveal a 2.8: 1 ratio of β to α anomer of 3'-fluoro-3'-deoxy-5'-O-acetylthymidine. The two nucleosides were further purified by silica gel flash-chromatography (10: 1 ethyl acetate-hexanes) to give 5'-O-acetyl FLT (71%, 65 mg).

1-(5-O-Acetyl-3-fluoro-2,3-dideoxy-β-D-erythropen-tofuranosyl) thymine. Physical and Spectral Data:

Physical data: White foam, $R_f$ 0.49 (10:1 ethyl acetate: hexanes).

¹H NMR: (300.1 MHz, CDCl₃) δ8.97 (s, 1H, NH on thymine); 7.24 (s, 1H, H-6); 6.34 (dd, 1H, J=8.8, 3.3, H-1'); 5.27, 5.12 (dd, 1H, J=53.45, 5.2, H-3'); 4.49, 4.43 (dt, 1H, J=25.9, 3.4, H-4'); 4.33 (qd, 2H, J-12.1, 3.9, H-5'); 2.68 (dtd, 1H, J=5.6, 6.0, 5.4, H-2'); (m acetate signal, 1H, H-2"); 2.12 (s, 3H, acetate); 1.92 (s, 3H, methyl at C-5).

¹³C NMR: (75.5 MHz, CDCl₃ δ170.05 (acetate (C=O); 163.91 (C-2 C=O); 150.37 (C-4 C=O); 134.70 (C-6); 111.33 (C-5); 94.57, 92.19 (J=179.8, C-3'); 85.32 (C-1'); 82.41, 82.06 (J=26.6, C-4'); 63.50, 63.36 (J=10.25, C-5'); 38.22, 37.94 (J=21.2, C-2"); 20.64 (acetate CH₃ ); 12.52 (C- 5 methyl) .

IR: (Neat, analyzed as anomeric mixture) 3190 (s, broad) , 3040 (s, broad), 2830 (m), 1750-1670 (rs, broad), 1470 (s) , 1375 (s), 1280 (vs), 1260-1230 (vs, broad), 1105 (vs), 1055 (s) , 1010(w), 980 (w), 910 (m), 875 (w), 805 (w), 780 (w), 750 (w).

MS: (low resolution FAB, analyzed as anomeric mixture) m/e 287.1 (M+H)⁺, 207.1 (5), 161.1 (12), 127.1 (100), 91.1 (15).

HRMS: ( FAB, analyzed as anomeric mixture) Calculated for C₁₄H₁₈OF₄: 287.1043. Found: 287.1046.

1-(5-O-Acetyl-3-fluoro-2,3-dideoxy-α-D-erythropentofuranosyl) thymine. Physical and Spectral Data:

Physical data: White foam, R_f 0.43 (10:1 ethyl acetate: hexanes).

¹H NMR: (300.1 MHz, CDCl₃) δ8.67 (s, 1H, NH on thymine); 7.24 (s, under solvent signal, 1H, H-6); 6.34 (dd, 1H, J=7.7, H-1'); 5.30, 5.12 (dd, 1H, J-53.4, 5.1, H-3'); 4.83, 4.75 (dt 1H, J=23.0, 4.5, H-4'); 4.13 (dd, 2H, J=4.5, 2.0, H-5'); 2.75 (ddd, 1H, J=40.3, 2.5, 7.8, H-2'); 2.42 (dd, 1H, J=16.1, 8.1, H-2'); 2.10 (s, 1H, acetate CH₃); 1.92 (s, 1H, C-5 CH₃).

¹³C NMR: (75.5 MHz, CDCl₃) δ170.20 (acetate C=O); 163.97 (C-2 C=O); 150.53 (C-4 C=O); 134.96 (C-6); 110.90 (C-5); 94.81, 92.45 (J=178.2, C-3'); 86.30 (C-1'); 84.56, 84.24 (J=24.2, C-4'); 63.25, 63.10 (J=11.3, C-5'); 39.30, 39.03 (J=20.4, C-2'); 20.69 (acetate CH₃); 12.60 (C-5 methyl).

IR: (Neat, analyzed as anomeric mixture) 3190 (s, broad), 3040 (s, broad), 2830 (m), 1750-1670 (vs, broad), 1470 (s), 1440(s), 1375 (s), 1280 (vs), 1260-1230 (vs, broad), 1105 (vs), 1055(s), 1010 (w), 980 (w), 910 (m), 875 (w), 805 (w), 780 (w), 750 (w).

MS: (low resolution FAB, analyzed as anomeric mixture) m/e 287.1 (M+H)⁺, 207.1 (5), 161.1 (12), 127.1 (100), 91.1 (15).

HRMS: (FAB, analyzed as anomeric mixture) Calculated for C₁₄H₁₈OF₄: 287.1043. Found: 287. 1046.

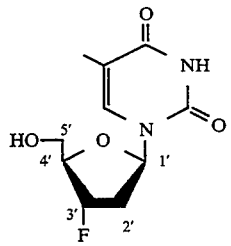

1-(3-Fluoro-2,3-dideoxy-β-D-erythropentofuranosyl)thymine.

To a round-bottomed flask equipped with a magnetic spinbar and rubber septum was added 40 mg (0.1399 mmoles) 1-(5-O-acetyl-3-fluoro-2,3-dideoxy-β-D-erythro -pentofuranosyl)thymine, 9.1 mg (0.1679 mmoles) NaOMe powder and MeOH (1.4 mL). The mixture was allowed to stir for @2 hours at room temperature. The solvent was removed in vacuo and the resulting residue was purified by silica gel flash-chromatography to yield 1-(3-fluoro-2,3-dideoxy-β-D-erythro-pentofuranosyl)thymine (85%, 29 mg) as a white powder.

1-(3-Fluoro-2,3-dideoxy-β-D-erythropentofuranosyl)thymine. Physical and Spectral Data:

Physical Data: White powder, mp. 175° C., R_f 0.39 (10:1 ethyl acetate).

¹H NMR: (300.1 MHz, d₆-DMSO) δ11.30 (s, 1H, NH on thymine); 7.64 (s, 1H, H-6); 6.16 (dd, 1H, J=5.6, 3.6); 5.33, 5.14 (dd with second d under another signal, 1H, J=51.8, 4.3, H-3'); 5.14 (t, 1H, OH); 4.13, 4.03 (dr, 1H, J=27.8, 3.7, H-4'); 3.56 (m, 2H, H-5'); 2.40-2.11 (m, 2H, H-2'); 1.72 (s, 3H, C-5 CH₃ ).

¹³C NMR: (75.5 MHz, CDCl₃) δ163.66 (C-2 C=O); 150.49 (C-4 C=O); 135.76 (C-6); 109.79 (C-5); 96.02, 93.71 (J=173.85, C-3'); 84.95, 84.65 (J=22.8, C-4'); 83.74 (C-1'); 60.95, 60.81 (J=11.0, C-5'); 37.07, 36.80 (J=20.3, C-2'); 12.26 (C-5 CH₃.

MS: (low resolution FAB) m/e 245 (M+H)⁺, 217(5), 149(20), 103(30). m/e 251 (M+Li) ⁺, 107 (20), 89 (30).

D. Preparation of 2'-deoxynucleosides containing 3'-β substituents

Figure 2:
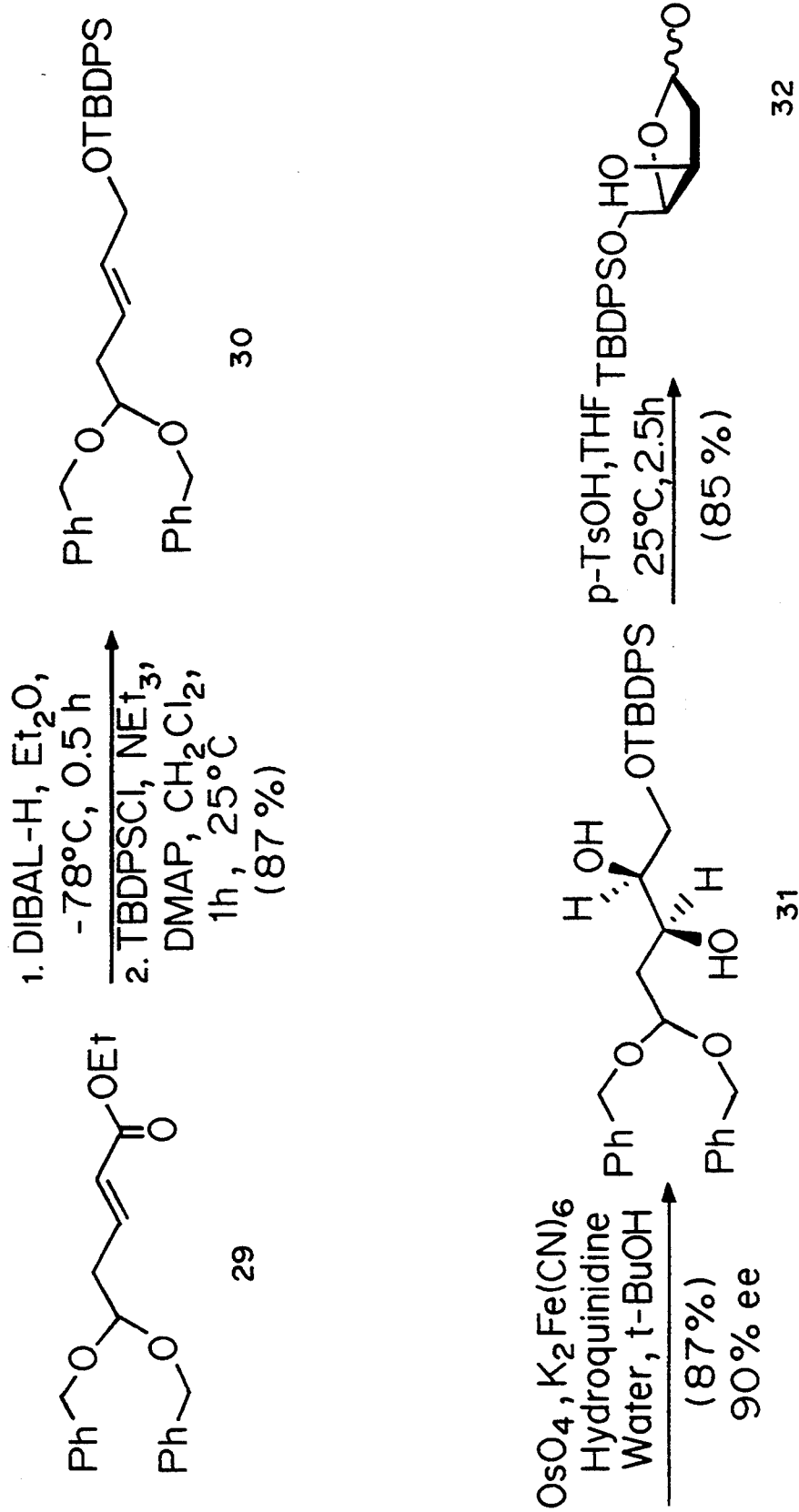
FIG. 2 is an illustration of the preparation of a lyxose carbohydrate by the asymmetric dihydroxylation of the tert-butyldiphenylsilyl derivative of 5,5-(diprotected oxy)-2E-penten-1-ol, followed by the stereoselective cyclization of the dihydroxylated product to a 2'-deoxynucleoside in which the 3'-hydroxyl group of the carbohydrate is in the β, or lyxose, configuration.

In an alternative embodiment, as shown in FIGS. 1 and 2, a lyxose derivative of a 2'-deoxynucleoside can be prepared by: (1) asymmetric dihydroxylation of a 5,5-(diprotected oxy)-2E-pentanoate or penten-1-(protected)-ol to form the corresponding 5,5-di(protected-oxy)-2(R),3(S)-dihydroxy-penten-1-(protected)-ol or -pentenoate; (2) stereoselective cyclization to a carbohydrate in which the 3-hydroxyl group is in the β, or lyxose, configuration; and then (3) addition of the heterocyclic base to the carbohydrate. The asymmetric dihydroxylation is conveniently carried out using osmium tetroxide and potassium ferricyanide. See Jacobsen, et al., J. Am. Chem. Soc. 110, 1968 (1988); Kwong, et al., Tet. Letters 31, 2999 (1990). The ester in the pentanoate can be reduced before or after the dihydroxylation step. The cyclization is carried out under acidic conditions as described in detail above.

Figure 3:
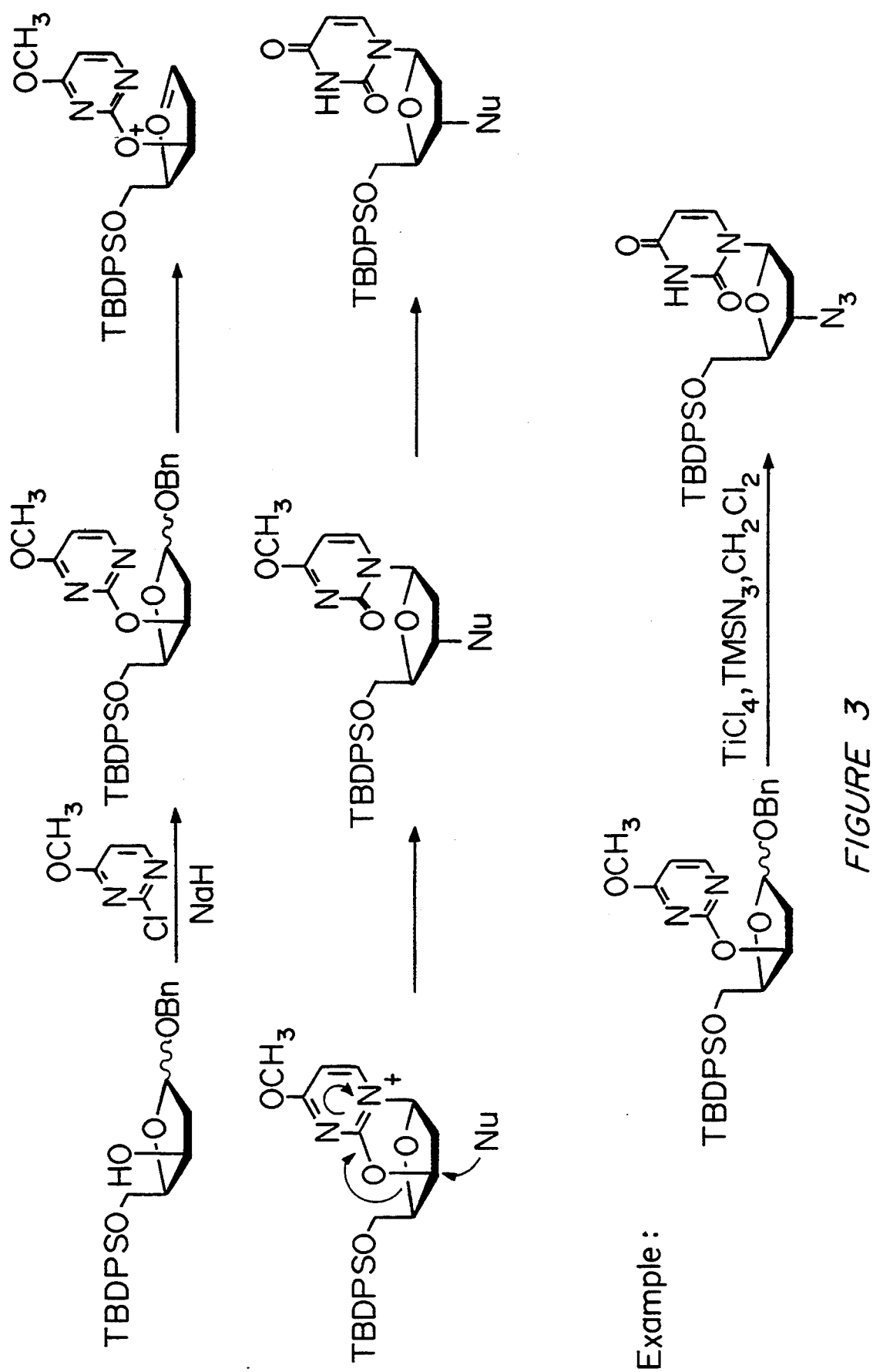
FIG. 3 is an illustration of the addition of 1-chloro-3-methoxypyrimidine to the 3-β-position of a lyxose carbohydrate, followed by simultaneous addition of a nucleophile to the 3-α-position of the carbohydrate and transfer of the pyrimidine to the 1-β-position.
Figure 4:
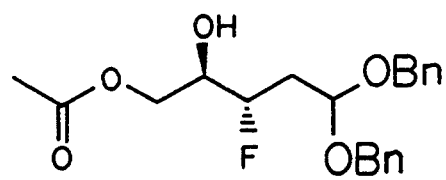
FIG. 4 is an illustration of the chemical structures of 5,5-dibenzyloxy-3(S)-fluoro-2(R)-hydroxyl-1-O-acetyl-pentane (compound 33), 1-benzyloxy-3-fluoro-4-methylene(O-protecting group)furan (compound 34); and 5-benzyloxy-5-thymine-3(S)-fluoro-1-O-acetyl-pentanol (compound 35).
Figure 4:
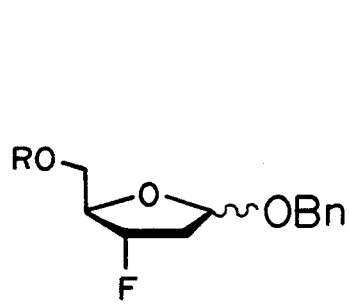
Figure 4:
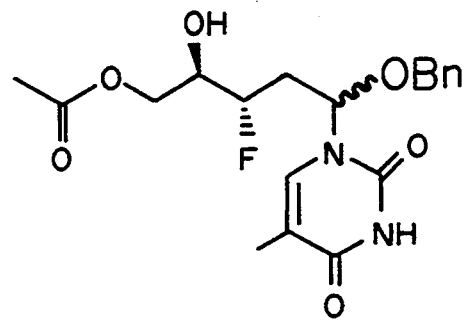

In an alternative embodiment, the heterocyclic base is added before cyclization (to the penten-1-ol or the dihydroxylated derivative) under Vorbruggen conditions also as described above. In another embodiment, after formation of the cyclized carbohydrate, as shown in FIG. 3, the base can be added to the 3-β-position, and then transferred to the 1-β-position in conjunction with addition of a nucleophile to the 3-β-α-position.

This approach to the preparation of 2'-deoxynucleosides containing 3'-β substituents is illustrated in further detail in the following working examples of the preparation of a mixture of 1-(α and β)-benzyloxy-3-β-hydroxyl-4-hydroxymethyltetrahydrofuran, that can be condensed with a heterocyclic base under conditions as described above. The compounds are numbered as illustrated in FIGS. 1 and 2.

Example 3 Preparation of a mixture of 1-(α and β)-benzyloxy-3-β-hydroxyl-4-hydroxymethyltetrahydrofuran To a round bottom flask was added 1.5 grams (0.0044 m) of ethyl 5,5-(dibenzyloxy)-2E-pentanoate (compound 25), 0.55 grams (0.0011 mole) of dihydroquinidine-p-chlorobenzoate, 436 grams (0.0132 mol) of potassium ferricyanide, 1.83 grams (0.0132 m) of potassium carbonate, and 0.23 ml (0.000088 m in toluene) of osmium tetroxide to a solution of 40 ml of water and 40 ml of t-butanol. The solution was stirred at room temperature for 20 hours, and then quenched with sodium metabisulfite. The solvent was removed in vacuo, and the residue extracted three times with ether to provide 1.3 grams of crude product (compound 26, 5,5-dibenzyloxy-2(S),3(R)-dihydroxypentanoate).

To a round bottom flask was added ethyl 5,5-dibenzyloxy-2(S),3(R)-dihydroxypentanoate (0.0085 m, 3.2 gram) and p-toluene sulfonic acid (0.0085 m, 1.6 gram) at 25° C. in 85 ml of THF. This mixture was stirred for 2 hours and then quenched with sodium bicarbonate and filtered. The solvent was removed in vacuo, and the crude product then reduced with sodium borohydride in dry ethanol to provide a 68% yield of a mixture of 1-(α and β)-benzyloxy-3-β-hydroxyl-4-hydroxymethyltetrahydrofuran.

Example 4 Alternative preparation of mixture of 1-(α and β)-benzyloxy-3-β-hydroxyl-4-hydroxymethyltetrahydrofuran Compound 29 (5,5-dibenzyloxy-2E-pentanoate) was reduced to the corresponding allylic alcohol as described above, and the terminal hydroxyl group then converted to the t-butyldiphenyl ether to provide compound 30 in 87% yield. Compound 30 (8.1 grams, 0.0151 m), dihydroxyquinidine p-chlorobenzoate (0.76 grams, 0.0151 m), potassium ferricyanide (14.9 grams, 0.0453 m), potassium carbonate (6.3 grams, 0.0453 m), and osmium tetroxide (0.77 ml, 0.0003 m in toluene) were mixed in a solution of 75 ml of t-butanol and 75 ml of water. The solution was stirred for 24 hours at room temperature and then quenched with sodium metabisulfite. The solvent was removed in vacuo, and the residue extracted three times with ether to provide 7.5 grams of crude product (compound 31). Compound 31 (5.2 grams, 0.0091 m) and 1.7 grams (0.0091 m) of p-toluenesulfonic acid were dissolved in 90 ml of THF at 0° C. The solution was allowed to warm to room temperature over 30 minutes, at which point thin layer chromatography indicated the absence of starting material. The reaction was quenched with sodium carbonate, and the solvent removed in vacuo. The residue was dissolved in excess ether and extracted three times with sodium carbonate, and then once with brine, to produce 4.92 grams of compound 32, a mixture of the 4-t-butyldiphenylether of 1-(α and β)-benzyloxy-3-β-hydroxyl-4-hydroxymethyltetrahydrofuran.

This invention has been described with reference to its preferred embodiments. Variations and modifications of the process for the preparation of 3'-substituted-2',3'-dideoxynucleosides and 2'-deoxynucleosides will be obvious to those skilled in the art from the foregoing detailed description of the invention. It is intended that all of these variations and modifications be included within the scope of the appended claims.

We claim:

1. A process for the preparation of a 3'-fluoro-2',3'-dideoxynucleoside comprising:
cyclizing a 5-(protected)oxy-5-(heterocyclic base)-3(S)-fluoro-1,2-(S)-pentanediol by exposing the pentanediol to a compound selected from a Lewis acid and a protic acid under kinetic conditions to form a 3'-α-fluoro-2',3'-dideoxy-β-anomeric nucleoside.

2. The process of claim 1 wherein the heterocyclic base is selected from the group consisting of purines and pyrimidines.
3. The process of claim 1 wherein the heterocyclic base is thymine.
4. The process of claim 1 wherein the heterocyclic base is uracil.
5. The process of claim 1 wherein the heterocyclic base is cytosine.
6. The process of claim 1 wherein the 5-(protecting) group is acetyl.
7. The process of claim 1 wherein the 5-(protecting) group is benzoyl.
8. The process of claim 1 further comprising preparing 5-(protected)oxy,5-(heterocyclic base)-3(S)-fluoro-1,2-(S)-pentanediol from 5,5-di(protected)oxy-2E-penten-1-ol comprising the steps of:
epoxidizing the 5,5-di(protected)oxy-2E-penten-1-ol to the corresponding 2(S),3(R)-epoxy alcohol;
reacting the epoxy alcohol with Bu$_4$NH$_2$F$_3$ to provide a 3(S)-fluoro-5,5-di(protected)oxy-1,2(S)-pentanediol; and then
substituting a heterocyclic base for the hydroxyl group in the 5-position of 3(S)-fluoro-5,5-di(protected)oxy-1,2-(S)-pentanediol.
9. The process of claim 8 wherein the hydroxyl moiety in the 2(S),3(R)-epoxy alcohol is protected with an oxygen protecting group prior to reaction with the Bu$_4$NH$_2$F$_3$.
10. The process of claim 8 wherein the epoxidation is performed with D-(−)-dialkyl tartrate, titanium alkoxide, and an organic hydroperoxide.
11. The process of claim 10 wherein the organic hydroperoxide is selected from the group consisting of tertbutyl hydroperoxide and cumene hydroperoxide.
12. The process of claim 10 wherein the epoxidation is carried out in the presence of zeolite molecular sieves.
13. The process of claim 10 wherein the dialkyl tartrate is selected from the group consisting of diethyl tartrate, dicyclohexyltartrate, and dicyclododecyl tartrate.
14. The process of claim 8 wherein the epoxidation is carried out with a reagent selected from the group consisting of metachloroperbenzoic acid, peracetic acid, perbenzoic acid, hydrogen peroxide, peroxytrifluoroacetic acid, monoperphthalic acid and dimethyl dioxirane.
15. The process of claim 1 wherein the protic acid is selected from the group consisting of sulfuric acid, hydrochloric acid, and halogenated acetic acids.
16. The process of claim 1 wherein the Lewis acid is selected from the group consisting of SnCl$_4$, ZnCl$_4$, TiCl$_4$, AlCl$_3$, FeCl$_3$, BF$_3$-diethyl ether, BCl$_3$, (CH$_3$)$_3$SiOSO$_2$CF$_3$, (CH$_3$)$_3$SiOSO$_2$C$_4$F$_9$, and (CH$_3$)$_3$SiClO$_4$, ROTiCl$_3$, (RO)$_2$TiCl$_2$, and (RO)$_3$TiCl, wherein R is an alkyl group.
17. The process of claim 8 wherein the 1,2-dihydroxyl groups are protected to form a 5,5-(diprotected)oxy-3-(S)-fluoro-1,2(S)-pentane-(protected diol) before addition of the heterocyclic base.
18. The process of claim 9 further comprising protecting nitrogen and oxygen moieties on the heterocycle before cyclization.
19. The process of claim 1 wherein the 3'-fluoro-2',3'-dideoxynucleoside is 3'-fluoro-3'-deoxythymidine.
20. The process of claim 10 wherein the 3'-fluoro-2',3'-dideoxynucleoside is 3'-fluoro-3'-deoxythymidine.
21. The process of claim 1 wherein the 3'-fluoro-2',3'-dideoxynucleoside is 3'-fluoro-2',3'-dideoxyuridine.
22. The process of claim 10 wherein the 3'-fluoro-2',3'-dideoxynucleoside is 3'-fluoro-3'-deoxyuridine.

* * * * *